United States Patent
Nakada et al.

(10) Patent No.: US 11,884,741 B2
(45) Date of Patent: Jan. 30, 2024

(54) METHOD FOR IMPROVING THERMAL STABILITY OF ANTIBODY AND METHOD FOR PRODUCING MODIFIED ANTIBODY

(71) Applicant: SYSMEX CORPORATION, Kobe (JP)

(72) Inventors: Tomofumi Nakada, Kobe (JP); Nobuyuki Ide, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 254 days.

(21) Appl. No.: 17/181,068

(22) Filed: Feb. 22, 2021

(65) Prior Publication Data

US 2021/0347910 A1 Nov. 11, 2021

(30) Foreign Application Priority Data

Feb. 25, 2020 (JP) ................. 2020-029711

(51) Int. Cl.
| | |
|---|---|
| C07K 16/32 | (2006.01) |
| C07K 16/00 | (2006.01) |
| C07K 16/28 | (2006.01) |
| C07K 1/22 | (2006.01) |
| C07K 1/34 | (2006.01) |

(52) U.S. Cl.
CPC ............ *C07K 16/32* (2013.01); *C07K 16/005* (2013.01); *C07K 16/2827* (2013.01); *C07K 1/22* (2013.01); *C07K 1/34* (2013.01); *C07K 2317/24* (2013.01); *C07K 2317/55* (2013.01); *C07K 2317/565* (2013.01); *C07K 2317/94* (2013.01)

(58) Field of Classification Search
CPC .. C07K 16/32; C07K 16/005; C07K 16/2827; C07K 1/22; C07K 1/34; C07K 2317/24; C07K 2317/55; C07K 2317/565; C07K 2317/94
See application file for complete search history.

(56) References Cited

U.S. PATENT DOCUMENTS

| | | | |
|---|---|---|---|
| 9,371,371 B2 | 6/2016 | Kim et al. | |
| 2012/0094874 A1 | 4/2012 | Ruker et al. | |
| 2013/0303406 A1* | 11/2013 | Kim ..................... | A61P 43/00 435/254.2 |
| 2019/0040119 A1 | 2/2019 | Ide et al. | |

FOREIGN PATENT DOCUMENTS

| | | | |
|---|---|---|---|
| EP | 3437657 A1 | 2/2019 | |
| GB | 2405873 A | 3/2005 | |
| JP | 2017-531620 A | 10/2017 | |
| JP | 2019-30231 A | 2/2019 | |
| WO | 2009/068631 A1 | 6/2009 | |
| WO | 2015/017548 A2 | 2/2015 | |
| WO | WO-2016040856 A2 * | 3/2016 | ......... A61K 47/6803 |

OTHER PUBLICATIONS

N. Martin Young et al: "Thermal stabilization of a single-chain Fv antibody fragment by introduction of a disulphide bond", FEBS Letters, Dec. 18, 1995, vol. 377, No. 2, pp. 135-139, Federation of European Biochemical Societies.
Dan Zabetakis et al: "Evaluation of Disulfide Bond Position to Enhance the Thermal Stability of a Highly Stable Single Domain Antibody", PLOS One, Dec. 19, 2014, vol. 9, No. 12, e115405, 14 pages.
The extended European search report dated Jul. 28, 2021 in a counterpart European patent application No. 21159129.2.
Marie-Paule Lefranc et al., "IMGT unique numbering for immunoglobulin and T cell receptor constant domains and Ig superfamily C-like domains", Developmental and Comparative Immunology, 2005, 29: 185-203.
Yoshihisa Hagihara et al., "Engineering disulfide bonds within an antibody", Biochimica et Biophysica Acta, 2014, 1844: 2016-2023.
Romain Rouet et al., "Stability engineering of the human antibody repertoire", FEBS Letters, 2014, 588: 269-277.
R. J. Poljak et al., "Three-Dimensional Structure of the Fab' Fragment of a Human Immunoglobulin at 2.8-A Resolution", Proc. Nat. Acad. Sci., 1973, 70(12): 3305-3310.
Dae Young Kim et al., "Disulfide linkage engineering for improving biophysical properties of human VH domains", Protein Engineering, Design & Selection, Aug. 30, 2012, pp. 581-589, vol. 25, No. 10.
Dirk Saerens et al., "Disulfide Bond Introduction for General Stabilization of Immunoglobulin Heavy-Chain Variable Domains", Journal of Molecular Biology, 2008, pp. 478-488, vol. 377, No. 2.
Dae Young Kim et al., "Evaluation of noncanonical Cys40-Cys55 disulfide linkage for stabilization of single-domain antibodies", Protein Science, 2019, pp. 881-888, vol. 28, No. 5.
Raiji Kawade et al., "Roles of the disulfide bond between the variable and the constant domains of rabbit immunoglobulin kappa chains in thermal stability and affinity", Protein Engineering, Design & Selection, May 30, 2018, pp. 243-247, vol. 31, No. 7-8.
Japanese Office Action dated Nov. 21, 2023 in a counterpart Japanese patent application No. 2020-029711.

* cited by examiner

*Primary Examiner* — Adam Weidner
*Assistant Examiner* — Laura Ann Essex
(74) *Attorney, Agent, or Firm* — Sughrue Mion, PLLC

(57) ABSTRACT

Disclosed is a method for producing a modified antibody, comprising: in a heavy chain of the antibody, changing at least one amino acid residue selected from the group consisting of 8th to 11th amino acid residues based on Kabat method to a cysteine residue, and changing at least one amino acid residue selected from the group consisting of 109th and 110th amino acid residues based on IMGT method to a cysteine residue; and recovering the modified antibody.

17 Claims, 9 Drawing Sheets

Specification includes a Sequence Listing.

FIG. 4

EVQLVESGGGLVQPGGSLRLSCAASGFNIKDTYIHWVRQAPGKGLEWVARIYPTNGYTRYADSVKGR
FTISADTSKNTAYLQMNSLRAEDTAVYYCSRWGGDGFYAMDYWGQGTLVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSC (SEQ ID NO: 1)

FIG. 5A

EVQLVESCGGLVQPGGSLRLSCAASGFNIKDTYIHWVRQAPGKGLEWVARIYPTNGYTRYADSVKGR
FTISADTSKNTAYLQMNSLRAEDTAVYYCSRWGGDGFYAMDYWGQGTLVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHCPSNTKVDKKVEPKSC (SEQ ID NO: 6)

FIG. 5B

EVQLVESCGGLVQPGGSLRLSCAASGFNIKDTYIHWVRQAPGKGLEWVARIYPTNGYTRYADSVKGR
FTISADTSKNTAYLQMNSLRAEDTAVYYCSRWGGDGFYAMDYWGQGTLVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKCSNTKVDKKVEPKSC (SEQ ID NO: 7)

FIG. 5C

EVQLVESCCGLVQPGGSLRLSCAASGFNIKDTYIHWVRQAPGKGLEWVARIYPTNGYTRYADSVKGR
FTISADTSKNTAYLQMNSLRAEDTAVYYCSRWGGDGFYAMDYWGQGTLVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHCPSNTKVDKKVEPKSC (SEQ ID NO: 8)

FIG. 5D

EVQLVESGCGLVQPGGSLRLSCAASGFNIKDTYIHWVRQAPGKGLEWVARIYPTNGYTRYADSVKGR
FTISADTSKNTAYLQMNSLRAEDTAVYYCSRWGGDGFYAMDYWGQGTLVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKCSNTKVDKKVEPKSC (SEQ ID NO: 9)

FIG. 6A

EVQLVESGGGLVQPGGSLRLSCAASGFNIK░░░░░WVRQAPGKGLEWVA░░░░░░░░░░░░░░░R
FTISADTSKNTAYLQMNSLRAEDTAVYYCSR░░░░░░░░░WGQGTLVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHCPSNTKVDKKVEPKSC   (SEQ ID NO: 10)

FIG. 6B

EVQLVESGGGLVQPGGSLRLSCAASGFNIK░░░░░WVRQAPGKGLEWVA░░░░░░░░░░░░░░░R
FTISADTSKNTAYLQMNSLRAEDTAVYYCSR░░░░░░░░░WGQGTLVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKCSNTKVDKKVEPKSC   (SEQ ID NO: 11)

FIG. 6C

EVQLVESGGGLVQPGGSLRLSCAASGFNIK░░░░░WVRQAPGKGLEWVA░░░░░░░░░░░░░░░R
FTISADTSKNTAYLQMNSLRAEDTAVYYCSR░░░░░░░░░WGQGTLVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKCSNTKVDKKVEPKSC   (SEQ ID NO: 12)

FIG. 6D

EVQLVESGGGVQPGGSLRLSCAASGFNIK░░░░░WVRQAPGKGLEWVA░░░░░░░░░░░░░░░R
FTISADTSKNTAYLQMNSLRAEDTAVYYCSR░░░░░░░░░WGQGTLVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKCSNTKVDKKVEPKSC(SEQ ID NO: 13)

FIG. 7

EVQLVESGGGLVQPGGSLRLSCAASGFNIKDTYIHWVRQAPGKGLEWVARIYPTNGYTRYADSVKGR
FTISADTSKNTAYLQMNSLRAEDTAVYYCSRWGGDGFYAMDYWGQGTLVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAPI
EKTISKAKGQPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK (SEQ ID NO: 14)

FIG. 8A

DIQMTQSPSSLSASVGDRVTITCRASQDVNTAVAWYQQKPGKAPKLLIYSASFLYSGVPSRFSGSRSG
TDFTLTISSLQPEDFATYYCQQHYTTPPTFGQGTKVEIKRTVAAPSVFIFPPSDEQLKSGTASVVCLLN
NFYPREAKVQWKVDNALQSGNSQESVTEQDSKDSTYSLSSTLTLSKADYEKHKVYACEVTHQGLSSP
VTKSFNRGEC (SEQ ID NO: 15)

FIG. 8B

DIQMTQSPSSLSASVGDRVTITCRASQDVNTAVAWYQQKPGKAPKLLIYSASFLYSGVPSRFSGSRSG
TDFTLTISSLQCEDFATYYCQQHYTTPPTFGQGTKVEIKRTVAAPSVFIFPPSDEQLKSGTASVVCLLN
NFYPREAKVQWKVDNALQSGNSQESVTEQDSKDQTYSLSSTLTLSKADYEKHKVYACEVTHQGLSLP
VTKSFNRGEC (SEQ ID NO: 16)

FIG. 9

QSLEESGGRLVTPGTPLTLTCTVSGFSLSSHAMSWVRQAPGKGLEWIGIISSTNTTANWAKGRFTI
SRTSTTVDLKIASPTTEDTATYFCARRSDDGYDDYGFNLWGPGTLVTVSSGQPKAPSVFPLAPCC
GDTPSSTVTLGCLVKGYLPEPVTVTWNSGTLTNGVRTFPSVRQSSGLYSLSSVVSVTSSSQPVTCNV
AHPATNTKVDKTVAPSTC (SEQ ID NO: 21)

FIG. 10A

QSLEESGGRLVTPGTPLTLTCTVSGFSLSSHAMSWVRQAPGKGLEWIGIISSSTNTYYANWVKGRFTI
SRTSTTVDLKIASPTTEDTATYFCARVRSDDGYGDYGFHIWGPGTLVTVSSGQPKAPSVFPLAPCC
GDTPSSTVTLGCLVKGYLPEPVTVTWNSGTLTNGVRTFPSVRQSSGLYSLSSVVSVTSSSQPVTCNV
AHCATNTKVDKTVAPSTC (SEQ ID NO: 22)

FIG. 10B

QSLEESGGRLVTPGTPLTLTCTVSGFSLSSHAMSWVRQAPGKGLEWIGIISSSTNTYYANWVKGRFTI
SRTSTTVDLKIASPTTEDTATYFCARVRSDDGYGDYGFHIWGPGTLVTVSSGQPKAPSVFPLAPCC
GDTPSSTVTLGCLVKGYLPEPVTVTWNSGTLTNGVRTFPSVRQSSGLYSLSSVVSVTSSSQPVTCNV
AHPCTNTKVDKTVAPSTC (SEQ ID NO: 23)

FIG. 10C

QSLEESGGRLVTPGTPLTLTCTVSGFSLSSHAMSWVRQAPGKGLEWIGIISSSTNTYYANWVKGRFTI
SRTSTTVDLKIASPTTEDTATYFCARVRSDDGYGDYGFHIWGPGTLVTVSSGQPKAPSVFPLAPCC
GDTPSSTVTLGCLVKGYLPEPVTVTWNSGTLTNGVRTFPSVRQSSGLYSLSSVVSVTSSSQPVTCNV
AHCATNTKVDKTVAPSTC (SEQ ID NO: 24)

FIG. 10D

QSLEESGGRLVTPGTPLTLTCTVSGFSLSSHAMSWVRQAPGKGLEWIGIISSSTNTYYANWVKGRFTI
SRTSTTVDLKIASPTTEDTATYFCARVRSDDGYGDYGFHIWGPGTLVTVSSGQPKAPSVFPLAPCC
GDTPSSTVTLGCLVKGYLPEPVTVTWNSGTLTNGVRTFPSVRQSSGLYSLSSVVSVTSSSQPVTCNV
AHPCTNTKVDKTVAPSTC (SEQ ID NO: 25)

FIG. 11A

QSLEESGGCLVTPGTPLTLTCTVSGFSLSSHAMSWVRQAPGKGLEWLGISSSTNTYYANWVKGRFTI
SRTSTTVDLKIASPTTEDTATYFCARVRSDDGYGDYGPFNIWGPGTLVTVSSGQPKAPSVFPLAPCC
GDTPSSTVTLGCLVKGYLPEPVTVTWNSGTLTNGVRTFPSVRQSSGLYSLSSVVSVTSSSQPVTCNV
AHCATNTKVDKTVAPSTC (SEQ ID NO: 26)

FIG. 11B

QSLEESGGCLVTPGTPLTLTCTVSGFSLSSHAMSWVRQAPGKGLEWLGISSSTNTYYANWVKGRFTI
SRTSTTVDLKIASPTTEDTATYFCARVRSDDGYGDYGPFNIWGPGTLVTVSSGQPKAPSVFPLAPCC
GDTPSSTVTLGCLVKGYLPEPVTVTWNSGTLTNGVRTFPSVRQSSGLYSLSSVVSVTSSSQPVTCNV
AHPCTNTKVDKTVAPSTC (SEQ ID NO: 27)

FIG. 11C

QSLEESGGRCVTPGTPLTLTCTVSGFSLSSHAMSWVRQAPGKGLEWLGISSSTNTYYANWVKGRFTI
SRTSTTVDLKIASPTTEDTATYFCARVRSDDGYGDYGPFNIWGPGTLVTVSSGQPKAPSVFPLAPCC
GDTPSSTVTLGCLVKGYLPEPVTVTWNSGTLTNGVRTFPSVRQSSGLYSLSSVVSVTSSSQPVTCNV
AHCATNTKVDKTVAPSTC (SEQ ID NO: 28)

FIG. 11D

QSLEESGGRCVTPGTPLTLTCTVSGFSLSSHAMSWVRQAPGKGLEWLGISSSTNTYYANWVKGRFTI
SRTSTTVDLKIASPTTEDTATYFCARVRSDDGYGDYGPFNIWGPGTLVTVSSGQPKAPSVFPLAPCC
GDTPSSTVTLGCLVKGYLPEPVTVTWNSGTLTNGVRTFPSVRQSSGLYSLSSVVSVTSSSQPVTCNV
AHPCTNTKVDKTVAPSTC (SEQ ID NO: 29)

FIG. 12A

ELVLTQTPPSLSASVGETVRIRC|ASEDIYSQMS|WYQQKPGKPPTLLIY|DASRLES|GVPPRFSGSGSG
TDYTLTIGGVQAEDAATYYC|QQYSYSRLT|FGAGTKVEIKRDPVAPSVLLFPPSKEELTTGTATIVCVA
NKFYPSDITVTWKVDGTTQQSGIENSKTPQSPEDNTYSLSSTLSLTSAQYNSHSVYTCEVVQGSASPI
VQSFNRGDC (SEQ ID NO: 30)

FIG. 12B

ELVLTQTPPSLSASVGETVRIRC|ASEDIYSQMS|WYQQKPGKPPTLLIY|DASRLES|GVPPRFSGSGSG
TDYTLTIGGVQCEDAATYYC|QQYSYSRLT|FGAGTKVEIKRDPVAPSVLLFPPSKEELTTGTATIVCVA
NKFYPSDITVTWKVDGTTQQSGIENSKTPQSPEDCTYSLSSTLSLTSAQYNSHSVYTCEVVQGSASPI
VQSFNRGDC (SEQ ID NO: 31)

SEQUENCE LISTING

<160> NUMBER OF SEQ ID NOS: 31

<210> SEQ ID NO 1
<211> LENGTH: 223
<212> TYPE: PRT
<213> ORGANISM: Artificial Sequence
<220> FEATURE:
<223> OTHER INFORMATION: Synthetic sequence, humanized antibody

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

<210> SEQ ID NO 2
<211> LENGTH: 5

```
<212> TYPE: PRT
<213> ORGANISM: Artificial Sequence
<220> FEATURE:
<223> OTHER INFORMATION: Synthetic sequence, humanized antibody

<400> SEQUENCE: 2

Asp Thr Tyr Ile His
1               5

<210> SEQ ID NO 3
<211> LENGTH: 17
<212> TYPE: PRT
<213> ORGANISM: Artificial Sequence
<220> FEATURE:
<223> OTHER INFORMATION: Synthetic sequence, humanized antibody

<400> SEQUENCE: 3

Arg Ile Tyr Pro Thr Asn Gly Tyr Thr Arg Tyr Ala Asp Ser Val Lys
1               5                   10                  15

Gly

<210> SEQ ID NO 4
<211> LENGTH: 11
<212> TYPE: PRT
<213> ORGANISM: Artificial Sequence
<220> FEATURE:
<223> OTHER INFORMATION: Synthetic sequence, humanized antibody

<400> SEQUENCE: 4

Trp Gly Gly Asp Gly Phe Tyr Ala Met Asp Tyr
1               5                   10

<210> SEQ ID NO 5
<211> LENGTH: 120
<212> TYPE: PRT
<213> ORGANISM: Artificial Sequence
<220> FEATURE:
<223> OTHER INFORMATION: Synthetic sequence, humanized antibody

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 6
<211> LENGTH: 223
<212> TYPE: PRT
<213> ORGANISM: Artificial Sequence
<220> FEATURE:
<223> OTHER INFORMATION: Synthetic sequence, modified antibody
```

-continued

<400> SEQUENCE: 6

```
Glu Val Gln Leu Val Glu Ser Cys Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Cys
        195                 200                 205

Pro Ser Asn Thr Lys Val Asp Lys Lys Val Glu Pro Lys Ser Cys
    210                 215                 220
```

<210> SEQ ID NO 7
<211> LENGTH: 223
<212> TYPE: PRT
<213> ORGANISM: Artificial Sequence
<220> FEATURE:
<223> OTHER INFORMATION: Synthetic sequence, modified antibody

<400> SEQUENCE: 7

```
Glu Val Gln Leu Val Glu Ser Cys Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125
```

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Cys Ser Asn Thr Lys Val Asp Lys Lys Val Glu Pro Lys Ser Cys
210                 215                 220
```

<210> SEQ ID NO 8
<211> LENGTH: 223
<212> TYPE: PRT
<213> ORGANISM: Artificial Sequence
<220> FEATURE:
<223> OTHER INFORMATION: Synthetic sequence, modified antibody

<400> SEQUENCE: 8

```
Glu Val Gln Leu Val Glu Ser Gly Cys Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Cys
        195                 200                 205

Pro Ser Asn Thr Lys Val Asp Lys Lys Val Glu Pro Lys Ser Cys
210                 215                 220
```

<210> SEQ ID NO 9
<211> LENGTH: 223
<212> TYPE: PRT
<213> ORGANISM: Artificial Sequence
<220> FEATURE:
<223> OTHER INFORMATION: Synthetic sequence, modified antibody

<400> SEQUENCE: 9

Glu Val Gln Leu Val Glu Ser Gly Cys Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Cys Ser Asn Thr Lys Val Asp Lys Lys Val Glu Pro Lys Ser Cys
210                 215                 220

<210> SEQ ID NO 10
<211> LENGTH: 223
<212> TYPE: PRT
<213> ORGANISM: Artificial Sequence
<220> FEATURE:
<223> OTHER INFORMATION: Synthetic sequence, modified antibody

<400> SEQUENCE: 10

Glu Val Gln Leu Val Glu Ser Gly Gly Cys Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Cys
        195                 200                 205

Pro Ser Asn Thr Lys Val Asp Lys Lys Val Glu Pro Lys Ser Cys
    210                 215                 220
```

<210> SEQ ID NO 11
<211> LENGTH: 223
<212> TYPE: PRT
<213> ORGANISM: Artificial Sequence
<220> FEATURE:
<223> OTHER INFORMATION: Synthetic sequence, modified antibody

<400> SEQUENCE: 11

```
Glu Val Gln Leu Val Glu Ser Gly Gly Cys Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
        195                 200                 205

Cys Ser Asn Thr Lys Val Asp Lys Lys Val Glu Pro Lys Ser Cys
    210                 215                 220
```

<210> SEQ ID NO 12
<211> LENGTH: 223
<212> TYPE: PRT
<213> ORGANISM: Artificial Sequence
<220> FEATURE:
<223> OTHER INFORMATION: Synthetic sequence, modified antibody

<400> SEQUENCE: 12

Glu Val Gln Leu Val Glu Ser Gly Gly Gly Cys Val Gln Pro Gly Gly

```
1               5                   10                  15
Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
            50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Cys
            195                 200                 205

Pro Ser Asn Thr Lys Val Asp Lys Lys Val Glu Pro Lys Ser Cys
210                 215                 220

<210> SEQ ID NO 13
<211> LENGTH: 223
<212> TYPE: PRT
<213> ORGANISM: Artificial Sequence
<220> FEATURE:
<223> OTHER INFORMATION: Synthetic sequence, modified antibody

<400> SEQUENCE: 13

Glu Val Gln Leu Val Glu Ser Gly Gly Gly Cys Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
            50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
```

```
                145                 150                 155                 160
Trp Asn Ser Gly Ala Leu Thr Ser Gly Val His Thr Phe Pro Ala Val
                    165                 170                 175
Leu Gln Ser Ser Gly Leu Tyr Ser Leu Ser Val Val Thr Val Pro
                    180                 185                 190
Ser Ser Ser Leu Gly Thr Gln Thr Tyr Ile Cys Asn Val Asn His Lys
                    195                 200                 205
Cys Ser Asn Thr Lys Val Asp Lys Lys Val Glu Pro Lys Ser Cys
        210                 215                 220

<210> SEQ ID NO 14
<211> LENGTH: 450
<212> TYPE: PRT
<213> ORGANISM: Artificial Sequence
<220> FEATURE:
<223> OTHER INFORMATION: Synthetic sequence, humanized antibody

<400> SEQUENCE: 14

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Val Val Thr Val Pro
                    180                 185                 190
Ser Ser Ser Leu Gly Thr Gln Thr Tyr Ile Cys Asn Val Asn His Lys
                    195                 200                 205
Pro Ser Asn Thr Lys Val Asp Lys Lys Val Glu Pro Lys Ser Cys Asp
        210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
```

```
                290                 295                 300
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 15
<211> LENGTH: 214
<212> TYPE: PRT
<213> ORGANISM: Artificial Sequence
<220> FEATURE:
<223> OTHER INFORMATION: Synthetic sequence, humanized antibody

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

```
                195                 200                 205

Phe Asn Arg Gly Glu Cys
    210

<210> SEQ ID NO 16
<211> LENGTH: 214
<212> TYPE: PRT
<213> ORGANISM: Artificial Sequence
<220> FEATURE:
<223> OTHER INFORMATION: Synthetic sequence, modified antibody

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Cys
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Cys Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Leu Pro Val Thr Lys Ser
        195                 200                 205

Phe Asn Arg Gly Glu Cys
    210

<210> SEQ ID NO 17
<211> LENGTH: 11
<212> TYPE: PRT
<213> ORGANISM: Artificial Sequence
<220> FEATURE:
<223> OTHER INFORMATION: Synthetic sequence, humanized antibody

<400> SEQUENCE: 17

Arg Ala Ser Gln Asp Val Asn Thr Ala Val Ala
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Synthetic sequence, humanized antibody

<400> SEQUENCE: 18
```

```
Ser Ala Ser Phe Leu Tyr Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic sequence, humanized antibody

<400> SEQUENCE: 19

Gln Gln His Tyr Thr Thr Pro Pro Thr
1               5

<210> SEQ ID NO 20
<211> LENGTH: 110
<212> TYPE: PRT
<213> ORGANISM: Artificial Sequence
<220> FEATURE:
<223> OTHER INFORMATION: Synthetic sequence, humanized antibody

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65              70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val
            100                 105                 110

<210> SEQ ID NO 21
<211> LENGTH: 220
<212> TYPE: PRT
<213> ORGANISM: Oryctolagus cuniculus

<400> SEQUENCE: 21

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser His Ala
            20                  25                  30

Met Ser Trp Val Arg Gln Ala Pro Gly Lys Gly Leu Glu Trp Ile Gly
        35                  40                  45

Ile Ile Ser Ser Ser Thr Asn Thr Trp Tyr Ala Asn Trp Val Lys Gly
    50                  55                  60

Arg Phe Thr Ile Ser Arg Thr Ser Thr Thr Val Asp Leu Lys Ile Ala
65              70                  75                  80

Ser Pro Thr Thr Glu Asp Thr Ala Thr Tyr Phe Cys Ala Arg Val Arg
                85                  90                  95

Ser Asp Asp Gly Tyr Gly Asp Tyr Gly Pro Phe Asn Leu Trp Gly Pro
            100                 105                 110

Gly Thr Leu Val Thr Val Ser Ser Gly Gln Pro Lys Ala Pro Ser Val
        115                 120                 125
```

```
Phe Pro Leu Ala Pro Cys Cys Gly Asp Thr Pro Ser Ser Thr Val Thr
    130                 135                 140

Leu Gly Cys Leu Val Lys Gly Tyr Leu Pro Glu Pro Val Thr Val Thr
145                 150                 155                 160

Trp Asn Ser Gly Thr Leu Thr Asn Gly Val Arg Thr Phe Pro Ser Val
                165                 170                 175

Arg Gln Ser Ser Gly Leu Tyr Ser Leu Ser Ser Val Val Ser Val Thr
            180                 185                 190

Ser Ser Ser Gln Pro Val Thr Cys Asn Val Ala His Pro Ala Thr Asn
        195                 200                 205

Thr Lys Val Asp Lys Thr Val Ala Pro Ser Thr Cys
    210                 215                 220

<210> SEQ ID NO 22
<211> LENGTH: 220
<212> TYPE: PRT
<213> ORGANISM: Artificial Sequence
<220> FEATURE:
<223> OTHER INFORMATION: Synthetic sequence, modified antibody

<400> SEQUENCE: 22

Gln Ser Leu Glu Glu Ser Cys Gly Arg Leu Val Thr Pro Gly Thr Pro
1               5                   10                  15

Leu Thr Leu Thr Cys Thr Val Ser Gly Phe Ser Leu Ser Ser His Ala
            20                  25                  30

Met Ser Trp Val Arg Gln Ala Pro Gly Lys Gly Leu Glu Trp Ile Gly
        35                  40                  45

Ile Ile Ser Ser Ser Thr Asn Thr Trp Tyr Ala Asn Trp Val Lys Gly
50                  55                  60

Arg Phe Thr Ile Ser Arg Thr Ser Thr Thr Val Asp Leu Lys Ile Ala
65                  70                  75                  80

Ser Pro Thr Thr Glu Asp Thr Ala Thr Tyr Phe Cys Ala Arg Val Arg
            85                  90                  95

Ser Asp Asp Gly Tyr Gly Asp Tyr Gly Pro Phe Asn Leu Trp Gly Pro
            100                 105                 110

Gly Thr Leu Val Thr Val Ser Ser Gly Gln Pro Lys Ala Pro Ser Val
        115                 120                 125

Phe Pro Leu Ala Pro Cys Cys Gly Asp Thr Pro Ser Ser Thr Val Thr
    130                 135                 140

Leu Gly Cys Leu Val Lys Gly Tyr Leu Pro Glu Pro Val Thr Val Thr
145                 150                 155                 160

Trp Asn Ser Gly Thr Leu Thr Asn Gly Val Arg Thr Phe Pro Ser Val
                165                 170                 175

Arg Gln Ser Ser Gly Leu Tyr Ser Leu Ser Ser Val Val Ser Val Thr
            180                 185                 190

Ser Ser Ser Gln Pro Val Thr Cys Asn Val Ala His Cys Ala Thr Asn
        195                 200                 205

Thr Lys Val Asp Lys Thr Val Ala Pro Ser Thr Cys
    210                 215                 220

<210> SEQ ID NO 23
<211> LENGTH: 220
<212> TYPE: PRT
<213> ORGANISM: Artificial Sequence
<220> FEATURE:
<223> OTHER INFORMATION: Synthetic sequence, modified antibody
```

<400> SEQUENCE: 23

```
Gln Ser Leu Glu Glu Ser Cys Gly Arg Leu Val Thr Pro Gly Thr Pro
1               5                   10                  15

Leu Thr Leu Thr Cys Thr Val Ser Gly Phe Ser Leu Ser Ser His Ala
            20                  25                  30

Met Ser Trp Val Arg Gln Ala Pro Gly Lys Gly Leu Glu Trp Ile Gly
        35                  40                  45

Ile Ile Ser Ser Ser Thr Asn Thr Trp Tyr Ala Asn Trp Val Lys Gly
    50                  55                  60

Arg Phe Thr Ile Ser Arg Thr Ser Thr Thr Val Asp Leu Lys Ile Ala
65                  70                  75                  80

Ser Pro Thr Thr Glu Asp Thr Ala Thr Tyr Phe Cys Ala Arg Val Arg
                85                  90                  95

Ser Asp Asp Gly Tyr Gly Asp Tyr Gly Pro Phe Asn Leu Trp Gly Pro
            100                 105                 110

Gly Thr Leu Val Thr Val Ser Ser Gly Gln Pro Lys Ala Pro Ser Val
        115                 120                 125

Phe Pro Leu Ala Pro Cys Cys Gly Asp Thr Pro Ser Ser Thr Val Thr
    130                 135                 140

Leu Gly Cys Leu Val Lys Gly Tyr Leu Pro Glu Pro Val Thr Val Thr
145                 150                 155                 160

Trp Asn Ser Gly Thr Leu Thr Asn Gly Val Arg Thr Phe Pro Ser Val
                165                 170                 175

Arg Gln Ser Ser Gly Leu Tyr Ser Leu Ser Ser Val Val Ser Val Thr
            180                 185                 190

Ser Ser Ser Gln Pro Val Thr Cys Asn Val Ala His Pro Cys Thr Asn
        195                 200                 205

Thr Lys Val Asp Lys Thr Val Ala Pro Ser Thr Cys
    210                 215                 220
```

<210> SEQ ID NO 24
<211> LENGTH: 220
<212> TYPE: PRT
<213> ORGANISM: Artificial Sequence
<220> FEATURE:
<223> OTHER INFORMATION: Synthetic sequence, modified antibody

<400> SEQUENCE: 24

```
Gln Ser Leu Glu Glu Ser Gly Cys Arg Leu Val Thr Pro Gly Thr Pro
1               5                   10                  15

Leu Thr Leu Thr Cys Thr Val Ser Gly Phe Ser Leu Ser Ser His Ala
            20                  25                  30

Met Ser Trp Val Arg Gln Ala Pro Gly Lys Gly Leu Glu Trp Ile Gly
        35                  40                  45

Ile Ile Ser Ser Ser Thr Asn Thr Trp Tyr Ala Asn Trp Val Lys Gly
    50                  55                  60

Arg Phe Thr Ile Ser Arg Thr Ser Thr Thr Val Asp Leu Lys Ile Ala
65                  70                  75                  80

Ser Pro Thr Thr Glu Asp Thr Ala Thr Tyr Phe Cys Ala Arg Val Arg
                85                  90                  95

Ser Asp Asp Gly Tyr Gly Asp Tyr Gly Pro Phe Asn Leu Trp Gly Pro
            100                 105                 110

Gly Thr Leu Val Thr Val Ser Ser Gly Gln Pro Lys Ala Pro Ser Val
        115                 120                 125

Phe Pro Leu Ala Pro Cys Cys Gly Asp Thr Pro Ser Ser Thr Val Thr
```

```
                    130                 135                 140
Leu Gly Cys Leu Val Lys Gly Tyr Leu Pro Glu Pro Val Thr Val Thr
145                 150                 155                 160

Trp Asn Ser Gly Thr Leu Thr Asn Gly Val Arg Thr Phe Pro Ser Val
                    165                 170                 175

Arg Gln Ser Ser Gly Leu Tyr Ser Leu Ser Ser Val Val Ser Val Thr
                    180                 185                 190

Ser Ser Ser Gln Pro Val Thr Cys Asn Val Ala His Cys Ala Thr Asn
                    195                 200                 205

Thr Lys Val Asp Lys Thr Val Ala Pro Ser Thr Cys
                    210                 215                 220

<210> SEQ ID NO 25
<211> LENGTH: 220
<212> TYPE: PRT
<213> ORGANISM: Artificial Sequence
<220> FEATURE:
<223> OTHER INFORMATION: Synthetic sequence, modified antibody

<400> SEQUENCE: 25

Gln Ser Leu Glu Glu Ser Gly Cys Arg Leu Val Thr Pro Gly Thr Pro
1               5                   10                  15

Leu Thr Leu Thr Cys Thr Val Ser Gly Phe Ser Leu Ser Ser His Ala
                    20                  25                  30

Met Ser Trp Val Arg Gln Ala Pro Gly Lys Gly Leu Glu Trp Ile Gly
                    35                  40                  45

Ile Ile Ser Ser Ser Thr Asn Thr Trp Tyr Ala Asn Trp Val Lys Gly
50                  55                  60

Arg Phe Thr Ile Ser Arg Thr Ser Thr Val Asp Leu Lys Ile Ala
65                  70                  75                  80

Ser Pro Thr Thr Glu Asp Thr Ala Thr Tyr Phe Cys Ala Arg Val Arg
                    85                  90                  95

Ser Asp Asp Gly Tyr Gly Asp Tyr Gly Pro Phe Asn Leu Trp Gly Pro
                    100                 105                 110

Gly Thr Leu Val Thr Val Ser Ser Gly Gln Pro Lys Ala Pro Ser Val
                    115                 120                 125

Phe Pro Leu Ala Pro Cys Cys Gly Asp Thr Pro Ser Ser Thr Val Thr
                    130                 135                 140

Leu Gly Cys Leu Val Lys Gly Tyr Leu Pro Glu Pro Val Thr Val Thr
145                 150                 155                 160

Trp Asn Ser Gly Thr Leu Thr Asn Gly Val Arg Thr Phe Pro Ser Val
                    165                 170                 175

Arg Gln Ser Ser Gly Leu Tyr Ser Leu Ser Ser Val Val Ser Val Thr
                    180                 185                 190

Ser Ser Ser Gln Pro Val Thr Cys Asn Val Ala His Pro Cys Thr Asn
                    195                 200                 205

Thr Lys Val Asp Lys Thr Val Ala Pro Ser Thr Cys
                    210                 215                 220

<210> SEQ ID NO 26
<211> LENGTH: 220
<212> TYPE: PRT
<213> ORGANISM: Artificial Sequence
<220> FEATURE:
<223> OTHER INFORMATION: Synthetic sequence, modified antibody

<400> SEQUENCE: 26
```

```
Gln Ser Leu Glu Glu Ser Gly Gly Cys Leu Val Thr Pro Gly Thr Pro
1               5                   10                  15
Leu Thr Leu Thr Cys Thr Val Ser Gly Phe Ser Leu Ser Ser His Ala
            20                  25                  30
Met Ser Trp Val Arg Gln Ala Pro Gly Lys Gly Leu Glu Trp Ile Gly
        35                  40                  45
Ile Ile Ser Ser Ser Thr Asn Thr Trp Tyr Ala Asn Trp Val Lys Gly
50                  55                  60
Arg Phe Thr Ile Ser Arg Thr Ser Thr Thr Val Asp Leu Lys Ile Ala
65                  70                  75                  80
Ser Pro Thr Thr Glu Asp Thr Ala Thr Tyr Phe Cys Ala Arg Val Arg
                85                  90                  95
Ser Asp Asp Gly Tyr Gly Asp Tyr Gly Pro Phe Asn Leu Trp Gly Pro
            100                 105                 110
Gly Thr Leu Val Thr Val Ser Ser Gly Gln Pro Lys Ala Pro Ser Val
        115                 120                 125
Phe Pro Leu Ala Pro Cys Cys Gly Asp Thr Pro Ser Ser Thr Val Thr
    130                 135                 140
Leu Gly Cys Leu Val Lys Gly Tyr Leu Pro Glu Pro Val Thr Val Thr
145                 150                 155                 160
Trp Asn Ser Gly Thr Leu Thr Asn Gly Val Arg Thr Phe Pro Ser Val
                165                 170                 175
Arg Gln Ser Ser Gly Leu Tyr Ser Leu Ser Ser Val Val Ser Val Thr
            180                 185                 190
Ser Ser Ser Gln Pro Val Thr Cys Asn Val Ala His Cys Ala Thr Asn
        195                 200                 205
Thr Lys Val Asp Lys Thr Val Ala Pro Ser Thr Cys
    210                 215                 220

<210> SEQ ID NO 27
<211> LENGTH: 220
<212> TYPE: PRT
<213> ORGANISM: Artificial Sequence
<220> FEATURE:
<223> OTHER INFORMATION: Synthetic sequence, modified antibody

<400> SEQUENCE: 27

Gln Ser Leu Glu Glu Ser Gly Gly Cys Leu Val Thr Pro Gly Thr Pro
1               5                   10                  15
Leu Thr Leu Thr Cys Thr Val Ser Gly Phe Ser Leu Ser Ser His Ala
            20                  25                  30
Met Ser Trp Val Arg Gln Ala Pro Gly Lys Gly Leu Glu Trp Ile Gly
        35                  40                  45
Ile Ile Ser Ser Ser Thr Asn Thr Trp Tyr Ala Asn Trp Val Lys Gly
50                  55                  60
Arg Phe Thr Ile Ser Arg Thr Ser Thr Thr Val Asp Leu Lys Ile Ala
65                  70                  75                  80
Ser Pro Thr Thr Glu Asp Thr Ala Thr Tyr Phe Cys Ala Arg Val Arg
                85                  90                  95
Ser Asp Asp Gly Tyr Gly Asp Tyr Gly Pro Phe Asn Leu Trp Gly Pro
            100                 105                 110
Gly Thr Leu Val Thr Val Ser Ser Gly Gln Pro Lys Ala Pro Ser Val
        115                 120                 125
Phe Pro Leu Ala Pro Cys Cys Gly Asp Thr Pro Ser Ser Thr Val Thr
    130                 135                 140
```

Leu Gly Cys Leu Val Lys Gly Tyr Leu Pro Glu Pro Val Thr Val Thr
145                 150                 155                 160

Trp Asn Ser Gly Thr Leu Thr Asn Gly Val Arg Thr Phe Pro Ser Val
                165                 170                 175

Arg Gln Ser Ser Gly Leu Tyr Ser Leu Ser Ser Val Val Ser Val Thr
                180                 185                 190

Ser Ser Ser Gln Pro Val Thr Cys Asn Val Ala His Pro Cys Thr Asn
            195                 200                 205

Thr Lys Val Asp Lys Thr Val Ala Pro Ser Thr Cys
        210                 215                 220

<210> SEQ ID NO 28
<211> LENGTH: 220
<212> TYPE: PRT
<213> ORGANISM: Artificial Sequence
<220> FEATURE:
<223> OTHER INFORMATION: Synthetic sequence, modified antibody

<400> SEQUENCE: 28

Gln Ser Leu Glu Glu Ser Gly Gly Arg Cys Val Thr Pro Gly Thr Pro
1               5                   10                  15

Leu Thr Leu Thr Cys Thr Val Ser Gly Phe Ser Leu Ser Ser His Ala
                20                  25                  30

Met Ser Trp Val Arg Gln Ala Pro Gly Lys Gly Leu Glu Trp Ile Gly
            35                  40                  45

Ile Ile Ser Ser Ser Thr Asn Thr Trp Tyr Ala Asn Trp Val Lys Gly
        50                  55                  60

Arg Phe Thr Ile Ser Arg Thr Ser Thr Thr Val Asp Leu Lys Ile Ala
65                  70                  75                  80

Ser Pro Thr Thr Glu Asp Thr Ala Thr Tyr Phe Cys Ala Arg Val Arg
                85                  90                  95

Ser Asp Asp Gly Tyr Gly Asp Tyr Gly Pro Phe Asn Leu Trp Gly Pro
                100                 105                 110

Gly Thr Leu Val Thr Val Ser Ser Gly Gln Pro Lys Ala Pro Ser Val
            115                 120                 125

Phe Pro Leu Ala Pro Cys Cys Gly Asp Thr Pro Ser Ser Thr Val Thr
        130                 135                 140

Leu Gly Cys Leu Val Lys Gly Tyr Leu Pro Glu Pro Val Thr Val Thr
145                 150                 155                 160

Trp Asn Ser Gly Thr Leu Thr Asn Gly Val Arg Thr Phe Pro Ser Val
                165                 170                 175

Arg Gln Ser Ser Gly Leu Tyr Ser Leu Ser Ser Val Val Ser Val Thr
                180                 185                 190

Ser Ser Ser Gln Pro Val Thr Cys Asn Val Ala His Cys Ala Thr Asn
            195                 200                 205

Thr Lys Val Asp Lys Thr Val Ala Pro Ser Thr Cys
        210                 215                 220

<210> SEQ ID NO 29
<211> LENGTH: 220
<212> TYPE: PRT
<213> ORGANISM: Artificial Sequence
<220> FEATURE:
<223> OTHER INFORMATION: Synthetic sequence, modified antibody

<400> SEQUENCE: 29

Gln Ser Leu Glu Glu Ser Gly Gly Arg Cys Val Thr Pro Gly Thr Pro
1               5                   10                  15

Leu Thr Leu Thr Cys Thr Val Ser Gly Phe Ser Leu Ser His Ala
            20                  25                  30

Met Ser Trp Val Arg Gln Ala Pro Gly Lys Gly Leu Glu Trp Ile Gly
        35                  40                  45

Ile Ile Ser Ser Thr Asn Thr Trp Tyr Ala Asn Trp Val Lys Gly
50                  55                  60

Arg Phe Thr Ile Ser Arg Thr Ser Thr Val Asp Leu Lys Ile Ala
65                  70                  75                  80

Ser Pro Thr Thr Glu Asp Thr Ala Thr Tyr Phe Cys Ala Arg Val Arg
                85                  90                  95

Ser Asp Asp Gly Tyr Gly Asp Tyr Gly Pro Phe Asn Leu Trp Gly Pro
            100                 105                 110

Gly Thr Leu Val Thr Val Ser Ser Gly Gln Pro Lys Ala Pro Ser Val
            115                 120                 125

Phe Pro Leu Ala Pro Cys Cys Gly Asp Thr Pro Ser Ser Thr Val Thr
130                 135                 140

Leu Gly Cys Leu Val Lys Gly Tyr Leu Pro Glu Pro Val Thr Val Thr
145                 150                 155                 160

Trp Asn Ser Gly Thr Leu Thr Asn Gly Val Arg Thr Phe Pro Ser Val
                165                 170                 175

Arg Gln Ser Ser Gly Leu Tyr Ser Leu Ser Ser Val Val Ser Val Thr
            180                 185                 190

Ser Ser Ser Gln Pro Val Thr Cys Asn Val Ala His Pro Cys Thr Asn
            195                 200                 205

Thr Lys Val Asp Lys Thr Val Ala Pro Ser Thr Cys
            210                 215                 220

<210> SEQ ID NO 30
<211> LENGTH: 214
<212> TYPE: PRT
<213> ORGANISM: Oryctolagus cuniculus

<400> SEQUENCE: 30

Glu Leu Val Leu Thr Gln Thr Pro Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Met Ser Trp Tyr Gln Gln Lys Pro Gly Lys Pro Pro Thr Leu Leu Ile
        35                  40                  45

Tyr Gly Ala Ser Arg Leu Glu Ser Gly Val Pro Pro Arg Phe Ser Gly
    50                  55                  60

Ser Gly Ser Gly Thr Asp Tyr Thr Leu Thr Ile Gly Gly Val Gln Ala
65                  70                  75                  80

Glu Asp Ala Ala Thr Tyr Tyr Cys Leu Gly Gly Tyr Ser Tyr Ser Arg
                85                  90                  95

Thr Thr Phe Gly Ala Gly Thr Lys Val Glu Ile Lys Arg Asp Pro Val
            100                 105                 110

Ala Pro Ser Val Leu Leu Phe Pro Pro Ser Lys Glu Glu Leu Thr Thr
            115                 120                 125

Gly Thr Ala Thr Ile Val Cys Val Ala Asn Lys Phe Tyr Pro Ser Asp
            130                 135                 140

Ile Thr Val Thr Trp Lys Val Asp Gly Thr Thr Gln Gln Ser Gly Ile
145                 150                 155                 160

Glu Asn Ser Lys Thr Pro Gln Ser Pro Glu Asp Asn Thr Tyr Ser Leu

-continued

```
                165                 170                 175
Ser Ser Thr Leu Ser Leu Thr Ser Ala Gln Tyr Asn Ser His Ser Val
            180                 185                 190

Tyr Thr Cys Glu Val Val Gln Gly Ser Ala Ser Pro Ile Val Gln Ser
            195                 200                 205

Phe Asn Arg Gly Asp Cys
    210

<210> SEQ ID NO 31
<211> LENGTH: 214
<212> TYPE: PRT
<213> ORGANISM: Artificial Sequence
<220> FEATURE:
<223> OTHER INFORMATION: Synthetic sequence, modified antibody

<400> SEQUENCE: 31

Glu Leu Val Leu Thr Gln Thr Pro Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Met Ser Trp Tyr Gln Gln Lys Pro Gly Lys Pro Thr Leu Leu Ile
            35                  40                  45

Tyr Gly Ala Ser Arg Leu Glu Ser Gly Val Pro Pro Arg Phe Ser Gly
    50                  55                  60

Ser Gly Ser Gly Thr Asp Tyr Thr Leu Thr Ile Gly Gly Val Gln Cys
65                  70                  75                  80

Glu Asp Ala Ala Thr Tyr Tyr Cys Leu Gly Gly Tyr Ser Tyr Ser Arg
                85                  90                  95

Thr Thr Phe Gly Ala Gly Thr Lys Val Glu Ile Lys Arg Asp Pro Val
            100                 105                 110

Ala Pro Ser Val Leu Leu Phe Pro Pro Ser Lys Glu Glu Leu Thr Thr
            115                 120                 125

Gly Thr Ala Thr Ile Val Cys Val Ala Asn Lys Phe Tyr Pro Ser Asp
    130                 135                 140

Ile Thr Val Thr Trp Lys Val Asp Gly Thr Thr Gln Gln Ser Gly Ile
145                 150                 155                 160

Glu Asn Ser Lys Thr Pro Gln Ser Pro Glu Asp Cys Thr Tyr Ser Leu
                165                 170                 175

Ser Ser Thr Leu Ser Leu Thr Ser Ala Gln Tyr Asn Ser His Ser Val
            180                 185                 190

Tyr Thr Cys Glu Val Val Gln Gly Ser Ala Ser Pro Ile Val Gln Ser
            195                 200                 205

Phe Asn Arg Gly Asp Cys
    210
```

US 11,884,741 B2

METHOD FOR IMPROVING THERMAL STABILITY OF ANTIBODY AND METHOD FOR PRODUCING MODIFIED ANTIBODY

CROSS REFERENCE TO RELATED APPLICATIONS

This application claims priority from prior Japanese Patent Application No. 2020-029711, filed on Feb. 25, 2020, entitled "Modified antibody, method for producing the same, and method for improving thermal stability of antibody", the entire contents of which are incorporated herein by reference.

FIELD OF THE INVENTION

The present invention relates to a method for improving thermal stability of an antibody. The present invention relates to a method for producing a modified antibody.

BACKGROUND

Conventionally, a technique for improving thermal stability of an antibody by modifying an amino acid sequence of the antibody has been known. For example, U.S. Patent Application Publication No. 2019/0040119 describes that an antibody with improved thermal stability has been obtained by substituting 80th and 171st amino acid residues based on Kabat method in an amino acid sequence of a light chain of an antibody with cysteine residues.

An object of the present invention is to provide a novel antibody with improved thermal stability by modifying an amino acid sequence of a heavy chain, a method for producing the same, and a novel method for improving thermal stability of an antibody.

SUMMARY OF THE INVENTION

The scope of the present invention is defined solely by the appended claims, and is not affected to any degree by the statements within this summary.

The present invention provides a method for improving thermal stability of an antibody, comprising: in a heavy chain of the antibody, changing at least one amino acid residue selected from the group consisting of 8th to 11th amino acid residues based on Kabat method to a cysteine residue, and changing at least one amino acid residue selected from the group consisting of 109th and 110th amino acid residues based on IMGT method to a cysteine residue.

The present invention provides a method for producing a modified antibody, comprising: in a heavy chain of the antibody, changing at least one amino acid residue selected from the group consisting of 8th to 11th amino acid residues based on Kabat method to a cysteine residue, and changing at least one amino acid residue selected from the group consisting of 109th and 110th amino acid residues based on IMGT method to a cysteine residue; and recovering the modified antibody.

BRIEF DESCRIPTION OF THE DRAWINGS

FIG. 4 is a heavy chain of Fab fragment of wild type of humanized anti-HER2 antibody.

FIG. 5A is a heavy chain of Fab fragment of heavy-chain mutant type (8-109) of humanized anti-HER2 antibody.

FIG. 5B is a heavy chain of Fab fragment of heavy-chain mutant type (8-110) of humanized anti-HER2 antibody.

FIG. 5C is a heavy chain of Fab fragment of heavy-chain mutant type (9-109) of humanized anti-HER2 antibody.

FIG. 5D is a heavy chain of Fab fragment of heavy-chain mutant type (9-110) of humanized anti-HER2 antibody.

FIG. 6A is a heavy chain of Fab fragment of heavy-chain mutant type (10-109) of humanized anti-HER2 antibody.

FIG. 6B is a heavy chain of Fab fragment of heavy-chain mutant type (10-110) of humanized anti-HER2 antibody.

FIG. 6C is a heavy chain of Fab fragment of heavy-chain mutant type (11-109) of humanized anti-HER2 antibody.

FIG. 6D is a heavy chain of Fab fragment of heavy-chain mutant type (11-110) of humanized anti-HER2 antibody.

FIG. 7 is a heavy chain of wild type of humanized anti-HER2 antibody.

FIG. 8A is a light chain of wild type of humanized anti-HER2 antibody.

FIG. 8B is a light chain of light-chain mutant type (80-171) of humanized anti-HER2 antibody.

FIG. 9 is a heavy chain of Fab fragment of wild type of rabbit anti-CD80 antibody.

FIG. 10A is a heavy chain of Fab fragment of heavy-chain mutant type (8-109) of rabbit anti-CD80 antibody.

FIG. 10B is a heavy chain of Fab fragment of heavy-chain mutant type (8-110) of rabbit anti-CD80 antibody.

FIG. 10C is a heavy chain of Fab fragment of heavy-chain mutant type (9-109) of rabbit anti-CD80 antibody.

FIG. 10D is a heavy chain of Fab fragment of heavy-chain mutant type (9-110) of rabbit anti-CD80 antibody.

FIG. 11A is a heavy chain of Fab fragment of heavy-chain mutant type (10-109) of rabbit anti-CD80 antibody.

FIG. 11B is a heavy chain of Fab fragment of heavy-chain mutant type (10-110) of rabbit anti-CD80 antibody.

FIG. 11C is a heavy chain of Fab fragment of heavy-chain mutant type (11-109) of rabbit anti-CD80 antibody.

FIG. 11D is a heavy chain of Fab fragment of heavy-chain mutant type (11-110) of rabbit anti-CD80 antibody.

FIG. 12A is a light chain of wild type of rabbit anti-CD80 antibody.

FIG. 12B is a light chain of light-chain mutant type (80-171) of rabbit anti-CD80 antibody.

DETAILED DESCRIPTION OF THE PREFERRED EMBODIMENTS

Figure 1:
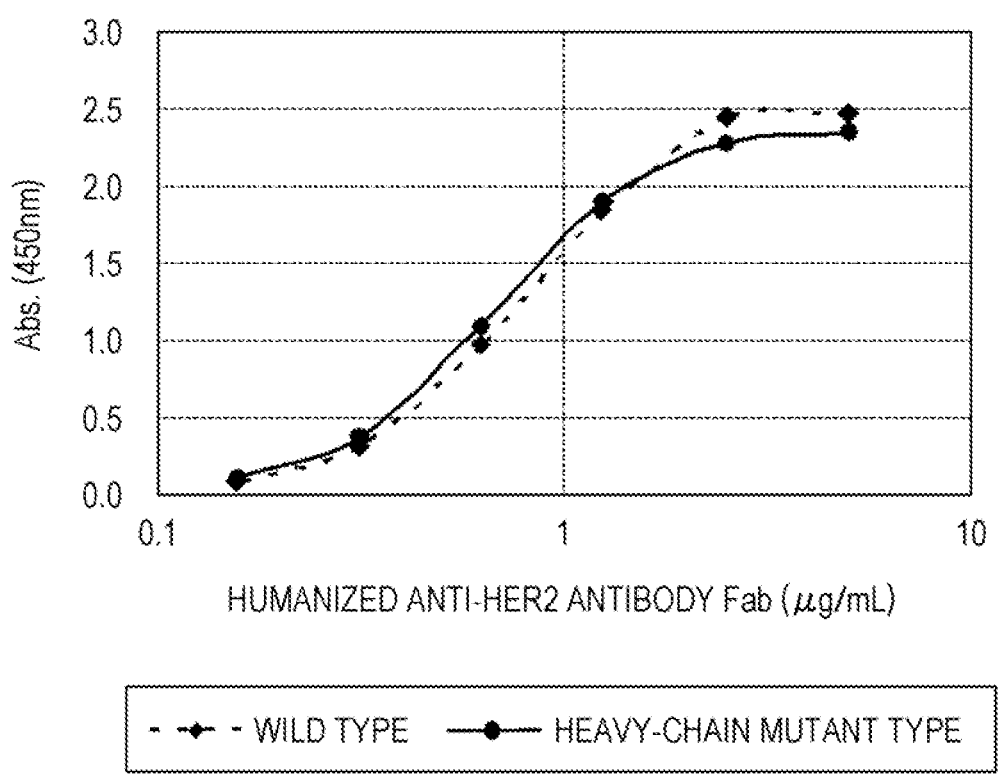
FIG. 1 is a graph showing results of analyzing affinities of a wild type and a heavy-chain mutant type (10-110) of a humanized anti-HER2 antibody (Fab) for an antigen by ELISA method.

The modified antibody of the present embodiment contains a heavy chain in which at least one amino acid residue selected from the group consisting of 8th to 11th amino acid residues based on Kabat method has been changed to a cysteine residue and at least one amino acid residue selected from the group consisting of 109th and 110th amino acid residues based on IMGT method has been changed to a cysteine residue. An antibody having an amino acid sequence before the above amino acid residues in the heavy chain are changed to cysteine residues is referred to as an "unmodified antibody".

In the present specification, in a heavy chain of an unmodified antibody, changing at least one amino acid residue selected from the group consisting of the 8th to 11th amino acid residues based on the Kabat method to a cysteine residue and changing at least one amino acid residue selected from the group consisting of the 109th and 110th amino acid residues based on the IMGT method to a cysteine residue are also referred to as "modifying a heavy chain" or "modification of a heavy chain". It is considered that, due to such modification of a heavy chain, a disulfide bond is formed between a cysteine residue present at at least one position selected from positions 8 to 11 based on the Kabat method and a cysteine residue present at at least one position selected from positions 109 and 110 based on the IMGT method. As a result of the formation of disulfide bond, it is considered that the modified antibody of the present embodiment has improved thermal stability as compared to the unmodified antibody. As described above, the modified antibody of the present embodiment is an antibody in which a heavy chain is artificially modified so as to improve thermal stability.

In the heavy chain of the antibody, the 8th to 11th amino acid residues based on the Kabat method are present in a variable region, and the 109th and 110th amino acid residues based on the IMGT method are present in a constant region. In the present specification, the phrase "based on Kabat method" for the heavy chain means that the amino acid residue in the variable region of the heavy chain is numbered in accordance with a numbering scheme by Kabat et al. (see Kabat E A et al., Sequences of Proteins of Immunological Interest, 5th ed. Public Health Service, National Institutes of Health, Bethesda, MD (1991), NIH Publication No. 91-3242). The phrase "based on IMGT method" for the heavy chain means that the amino acid residue in the constant region of the heavy chain is numbered in accordance with IMGT unique numbering by Lefranc et al. (see Lefranc M P. et al., Developmental and Comparative Immunology 29 (2005) 185-203).

In the present embodiment, the unmodified antibody is not particularly limited as long as it has a heavy chain in which either one or both of at least one amino acid residue selected from the group consisting of the 8th to 11th amino acid residues based on the Kabat method and at least one amino acid residue selected from the group consisting of the 109th and 110th amino acid residues based on the IMGT method is not a cysteine residue. The amino acid residue to be changed to a cysteine residue in the heavy chain of the unmodified antibody may be any amino acid residue other than a cysteine residue.

In the heavy chain of the unmodified antibody, when at least one amino acid residue selected from the group consisting of the 8th to 11th amino acid residues based on the Kabat method or at least one amino acid residue selected from the group consisting of the 109th and 110th amino acid residues based on the IMGT method is a cysteine residue, the cysteine residue may be left as it is. An antibody in which all of the 8th to 11th amino acid residues based on the Kabat method and the 109th and 110th amino acid residues based on the IMGT method are cysteine is not subject to modification of the present embodiment.

Examples of the method of changing the amino acid residue in the heavy chain of the unmodified antibody to a cysteine residue include substitution or insertion of an amino acid residue. Modification of the heavy chain by "substitution" herein means that an amino acid residue other than a cysteine residue present at at least one position selected from positions 8 to 11 based on the Kabat method and/or at least one position selected from positions 109 and 110 based on the IMGT method is changed to a cysteine residue.

Modification of the heavy chain by "insertion" herein means that a cysteine residue is newly added so as to be present at at least one position selected from positions 8 to 11 based on the Kabat method and/or at least one position selected from positions 109 and 110 based on the IMGT method. For example, when the 9th amino acid residue based on the Kabat method is changed to a cysteine residue and the 109th amino acid residue based on the IMGT method in the heavy chain of the unmodified antibody is changed to a cysteine residue by insertion, a cysteine residue may be added between the 9th and 10th amino acids based on the Kabat method, and a cysteine residue may be added between the 109th and 110th amino acids based on the IMGT method.

In a preferred embodiment, the modified antibody is an antibody obtained by modifying the heavy chain of the unmodified antibody by substitution. That is, it is preferable that the modified antibody contains a heavy chain in which at least one amino acid residue selected from the group consisting of the 8th to 11th amino acid residues based on the Kabat method has been changed to a cysteine residue by substitution. It is preferable that the modified antibody contains a heavy chain in which at least one amino acid residue selected from the group consisting of the 109th and 110th amino acid residues based on the IMGT method has been changed to a cysteine residue by substitution.

In the present embodiment, the unmodified antibody may be an antibody recognizing any antigen. The unmodified antibody may be an antibody having a natural amino acid sequence (wild-type antibody) or an artificially produced antibody. The artificially produced antibody refers to an antibody in which an amino acid sequence is artificially altered based on a means other than the modification of the heavy chain in the present embodiment. Examples of such an antibody include antibodies in which an amino acid sequence of CDR is altered, chimeric antibodies, humanized antibodies, bispecific antibodies, and the like.

In a preferred embodiment, the unmodified antibody is an antibody in which a base sequence of its gene is known or an antibody in which the base sequence can be confirmed. Specifically, it is an antibody in which the base sequence of the antibody gene is disclosed in a known database, or an antibody in which a hybridoma producing the antibody is available. Examples of such a database include GeneBank, abYsis, IMGT, and the like. When there is a hybridoma that produces an unmodified antibody, the base sequence of the antibody gene can be obtained by acquiring an antibody gene from the hybridoma by a known method and sequencing the base sequence.

The unmodified antibody and the modified antibody of the present embodiment may be an antibody derived from any animal. Such animals are preferably mammals such as, for example, humans, mice, rabbits, rats, pigs, sheep, goats, camels, cows and horses. Among them, humans, mice and rabbits are preferable.

Classes of the unmodified antibody and the modified antibody of the present embodiment may be any of IgG, IgA, IgM, IgD and IgE, and are preferably IgG. A subclass of IgG is not particularly limited, and may be any of IgG1, IgG2, IgG3 and IgG4. In the present embodiment, subclasses of the heavy chains of the unmodified antibody and the modified antibody are not particularly limited. The subclass of the heavy chain may be any of γ1, γ2, γ3 and γ4 when derived from humans, and may be any of γ1, γ2a, γ2b and γ3 when derived from mice.

The unmodified antibody may be in a form of an antibody fragment as long as it has the 8th to 11th amino acid residues based on the Kabat method and the 109th and 110th amino acid residues based on the IMGT method in the heavy chain. The modified antibody of the present embodiment may be in a form of an antibody fragment as long as it contains a cysteine residue introduced by modification of the heavy chain. Examples of such an antibody fragment include Fab, Fab', F(ab')2, reduced IgG (reduced IgG), and the like. Among them, Fab is particularly preferable.

In the present embodiment, the heavy chain of the modified antibody may have a full-length sequence of the heavy chain of the unmodified antibody, or may have a partial sequence of the heavy chain of the unmodified antibody. For example, when the unmodified antibody is a complete antibody (for example, IgG) and the modified antibody is an antibody fragment (for example, Fab), the heavy chain of the modified antibody in the form of an antibody fragment has a partial sequence of the heavy chain of the unmodified antibody.

As described above, the modified antibody of the present embodiment has improved thermal stability as compared to the unmodified antibody. Thermal stability of an antibody can be generally evaluated by a method of measuring an amount or ratio of antibody degenerated with thermal stress. Such a measuring method itself is known in the art, and examples thereof include measurement by a differential scanning calorimeter (DSC), a CD spectrum, a fluorescence spectrum, a Fourier transform infrared spectrophotometer (FTIR), and the like. In the present embodiment, it is preferable that the thermal stability of a modified antibody is evaluated by information obtained from measurement by DSC. Such information may be, for example, Tm (temperature at which heat capacity is maximum) or analysis peak itself.

In the present embodiment, Tm value of the modified antibody as measured by DSC is higher than Tm value of the unmodified antibody. For example, the Tm value of the modified antibody as measured by DSC is higher than the Tm value of the unmodified antibody by at least about 1° C., preferably at least about 2° C., and more preferably at least about 3° C.

Since the amino acid residue to be modified in the present embodiment is not an amino acid residue of CDR, it is considered that an affinity of the antibody for an antigen is not lowered to an extent that a practical problem occurs. The affinity of the antibody for an antigen may be evaluated by an immunological measurement method such as an ELISA method or may be evaluated by kinetic parameters (binding rate constant, dissociation rate constant and dissociation constant) in an antigen-antibody reaction. The kinetic parameters can be acquired by a surface plasmon resonance (SPR) technology.

In a preferred embodiment, the modified antibody contains a heavy chain in which at least one amino acid residue selected from the group consisting of the 9th and 10th amino acid residues based on the Kabat method and at least one amino acid residue selected from the group consisting of the 109th and 110th amino acid residues based on the IMGT method have been changed to cysteine residues. Among such modified antibodies, modified antibodies containing a heavy chain in which amino acid residues shown in any one of 1) to 3) below have been changed to cysteine residues are particularly preferable.

1) The 9th amino acid residue based on the Kabat method and the 109th amino acid residue based on the IMGT method;
2) The 9th amino acid residue based on the Kabat method and the 110th amino acid residue based on the IMGT method; and
3) The 10th amino acid residue based on the Kabat method and the 110th amino acid residue based on the IMGT method.

In the present embodiment, the antibody may be modified so that a disulfide bond is formed between a variable region and a constant region not only in the heavy chain but also in a light chain. That is, the modified antibody of the present embodiment may include a light chain in which 80th and 171st amino acid residues based on the Kabat method have been changed to cysteine residues. Such modification of a light chain itself is known and is described in U.S. Patent Application Publication No. 2019/0040119 (for reference, U.S. Patent Application Publication No. 2019/0040119 is incorporated herein by reference). The phrase "based on the Kabat method" for the light chain means that the amino acid residue in the variable region of the light chain is numbered in accordance with a numbering scheme by Kabat et al., and that the amino acid residue in the constant region of the light chain is numbered in accordance with an EU index by Kabat et al. The EU index is described in the above literature by Kabat et al. A subclass of the light chain is not particularly limited, but is preferably a κ chain.

In the present specification, in a light chain of an unmodified antibody, changing the 80th to 171st amino acid residues based on the Kabat method to cysteine residues is also referred to as "modifying a light chain" or "modification of a light chain". In the present embodiment, modification of the light chain of an unmodified antibody can be performed by substitution or insertion of an amino acid residue in the same manner as the modification of the heavy chain. In such a modified light chain, it is considered that a disulfide bond is formed between the cysteine residues present at positions 80 and 171 based on the Kabat method. In the modified antibody of the present embodiment having the modified light chain and heavy chain, thermal stability can be further improved by forming a disulfide bond in each of the light chain and the heavy chain.

As a specific example of the modified antibody of the present embodiment, each modified antibody of a humanized anti-HER2 antibody and a rabbit anti-CD80 antibody will be described. Hereinafter, the modified antibody of the present embodiment is also referred to as "heavy-chain mutant type (X-Y)". X is 8, 9, 10 or 11, and Y is 109 or 110. The "heavy-chain mutant type (X-Y)" represents a modified antibody in which an X-th amino acid residue based on the Kabat method has been changed to a cysteine residue and a Y-th amino acid residue based on the IMGT method in the heavy chain of the unmodified antibody has been changed to a cysteine residue.

An antibody having a light chain in which the 80th and 171st amino acid residues based on the Kabat method have been changed to cysteine residues and having an unmodified heavy chain is hereinafter also referred to as "light-chain mutant type (80-171)". A modified antibody of the present embodiment having a light-chain mutant type (80-171) light chain and a heavy-chain mutant type (X-Y) heavy chain is hereinafter also referred to as "light-chain/heavy-chain mutant type (80-171/X-Y)". X is 8, 9, 10 or 11, and Y is 109 or 110. The "light-chain/heavy-chain mutant type (80-171/X-Y)" represents a modified antibody in which the X-th amino acid residue and the Y-th amino acid residue in the heavy chain of the unmodified antibody have been changed to cysteine residues, and the 80th and 171st amino acid residues in the light chain of the unmodified antibody have been changed to cysteine residues.

FIG. 4 shows an amino acid sequence of a heavy chain in a Fab fragment of a wild type of the humanized anti-HER2 antibody (trastuzumab). In FIG. 4, an underlined section indicates a variable region, parts marked in gray indicate CDRs, residues surrounded by a square indicate 8th to 11th amino acid residues of a variable region based on the Kabat method, and residues surrounded by a square indicate 109th and 110th amino acid residues of a constant region based on the IMGT method. In the amino acid sequence shown in FIG. 4, the residues surrounded by a square in the constant region correspond to 208th and 209th, but in the IMGT method, these are numbered as the 109th and 110th amino acid residues.

The amino acid sequences of the CDRs and the variable region of the heavy chain of the humanized anti-HER2 antibody are as follows.

```
Heavy chain CDR1:
                                              (SEQ ID NO: 2)
DTYIH Heavy chain CDR2:
                                              (SEQ ID NO: 3)
RIYPTNGYTRYADSVKG Heavy chain CDR3:
                                              (SEQ ID NO: 4)
WGGDGFYAMDY Variable region:
                                              (SEQ ID NO: 5)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSS
```

FIGS. 5A-6D show amino acid sequences of heavy chains in Fab fragments of mutant types of the human anti-HER2 antibody. In FIGS. 5A-6D, underlined sections indicate variable regions, parts marked in gray indicate CDRs, residues surrounded by a square indicate X-th amino acid residues of variable regions based on the Kabat method, and residues surrounded by a square indicate Y-th amino acid residues of constant regions based on the IMGT method.

FIG. 7 shows a full-length sequence of a heavy chain of the wild type of the humanized anti-HER2 antibody. In FIG. 7, parts marked in gray indicate CDRs.

FIGS. 8A-8B show a full-length sequence of a light chain (κ) of the wild type of the humanized anti-HER2 antibody and an amino acid sequence of the mutant type thereof. In FIGS. 8A-8B, underlined sections indicate variable regions, parts marked in gray indicate CDRs, and residues surrounded by a square indicate 80th and 171st amino acid residues based on the Kabat method.

The amino acid sequences of the CDRs and the variable region of the light chain of the humanized anti-HER2 antibody are as follows.

```
Light chain CDR1:
                                              (SEQ ID NO: 17)
RASQDVNTAVA Light chain CDR2:
                                              (SEQ ID NO: 18)
SASFLYS Light chain CDR3:
                                              (SEQ ID NO: 19)
QQHYTTPPT Variable region:
                                              (SEQ ID NO: 20)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKRTV
```

FIG. 9 shows an amino acid sequence of a heavy chain in a Fab fragment of a wild type of the rabbit anti-CD80 antibody. In FIG. 9, an underlined section indicates a variable region, parts marked in gray indicate CDRs, residues surrounded by a square indicate 8th to 11th amino acid residues based on the Kabat method, and residues surrounded by a square indicate 109th and 110th amino acid residues based on the IMGT method. In the amino acid sequence shown in FIG. 9, the residues surrounded by a square in the variable region correspond to 7th to 10th, but in the case of rabbit antibody, numbering starts from 2nd in the Kabat method, so the residues surrounded by a square are the 8th to 11th amino acid residues based on the Kabat method. In the amino acid sequence shown in FIG. 9, the residues surrounded by a square in the constant region correspond to 205th and 206th, but in the IMGT method, these are numbered as the 109th and 110th amino acid residues.

FIGS. 10A-11D show amino acid sequences of heavy chains in Fab fragments of mutant types of the rabbit anti-CD80 antibody. In FIGS. 10A-11D, underlined sections indicate variable regions, parts marked in gray indicate CDRs, residues surrounded by a square indicate X-th amino acid residues based on the Kabat method, and residues surrounded by a square indicate Y-th amino acid residues based on the IMGT method. X is 8, 9, 10 or 11, and Y is 109 or 110.

FIGS. 12A-12B show a full-length sequence of a light chain (κ) of the wild type of the rabbit anti-CD80 antibody and an amino acid sequence of the mutant type thereof. In FIGS. 12A-12B, underlined sections indicate variable regions, parts marked in gray indicate CDRs, and residues surrounded by a square indicate 80th and 171st amino acid residues based on the Kabat method. In the amino acid sequences shown in FIGS. 12A-12B, the residues surrounded by a square in the constant region correspond to 172nd, but the residues are 171st amino acid residues in the Kabat method, due to length of the CDRs.

A use method of the modified antibody of the present embodiment is not particularly different from that of the unmodified antibody. The modified antibody can be used for various tests and research, antibody drugs and the like, as well as the unmodified antibody. The modified antibody of the present embodiment may be modified with a labeling substance or the like known in the art.

In the method for improving thermal stability of an antibody of the present embodiment (hereinafter, also referred to as "method for improving thermal stability"), in a heavy chain of the antibody, at least one amino acid residue selected from the group consisting of the 8th to 11th amino acid residues based on the Kabat method is changed to a cysteine residue and at least one amino acid residue selected from the group consisting of the 109th and 110th amino acid residues based on the IMGT method is changed to a cysteine residue. Due to the modification of the heavy chain, the thermal stability of the antibody improves as compared to that of the unmodified antibody. That is, the antibody in which the heavy chain is modified by the method for improving thermal stability of the present embodiment is the same as the modified antibody of the present embodiment described above.

The antibody targeted by the method for improving thermal stability of the present embodiment is the same as the unmodified antibody described above. Examples of the method of changing the amino acid residue in the heavy chain of the unmodified antibody to a cysteine residue include substitution or insertion of an amino acid residue. Substitution and insertion of an amino acid residue can be carried out by known methods such as DNA recombination technology and other molecular biological techniques. For example, when there is a hybridoma that produces an unmodified antibody, as shown in Example 1 described later, RNA extracted from the hybridoma is used to synthesize each of a polynucleotide encoding the light chain and a polynucleotide encoding the heavy chain, by a reverse transcription reaction and a RACE (Rapid Amplification of cDNA ends) method. The polynucleotide encoding the heavy chain is amplified by PCR method using a primer for modifying the heavy chain to obtain a polynucleotide encoding a modified heavy chain. For example, when substituting the 9th amino acid residue based on the Kabat method with a cysteine residue and substituting the 109th amino acid residue based on the IMGT method in the heavy chain of the unmodified antibody with a cysteine residue, the polynucleotide encoding the heavy chain is amplified by the PCR method using a primer for substituting those amino acid residues with cysteine residues to obtain a polynucleotide encoding a heavy chain having a cysteine residue at position 9 based on the Kabat method and having a cysteine residue at position 109 based on the IMGT method. By incorporating the obtained polynucleotide into an expression vector known in the art, together with a polynucleotide encoding the light chain of the unmodified antibody, an expression vector containing a polynucleotide encoding the modified antibody of the present embodiment is obtained.

The polynucleotide encoding the light chain and the polynucleotide encoding the heavy chain may be incorporated into one expression vector or may be separately incorporated into two expression vectors. The type of the expression vector is not particularly limited, and it may be an expression vector for mammalian cells or an expression vector for *E. coli*. By transforming or transfecting the obtained expression vector into an appropriate host cell (for example, mammalian cell or *E. coli*), a modified antibody can be obtained.

When there is no hybridoma that produces an unmodified antibody, an antibody-producing hybridoma may be prepared by known methods such as those described in, for example, Kohler and Milstein, Nature, vol. 256, p. 495-497, 1975. Alternatively, RNA obtained from peripheral blood or spleen of an animal such as a mouse or rabbit immunized with a predetermined antigen may be used. When RNA obtained from peripheral blood or spleen is used, cDNA may be synthesized from the RNA and a Fab phage library may be prepared from the obtained cDNA, as shown in Example 1 described later. Using this library, a polynucleotide encoding Fab as an unmodified antibody can be obtained by a phage display method or the like. The obtained polynucleotide is amplified by the PCR method as described above, so that a polynucleotide encoding Fab as the modified antibody of the present embodiment can be obtained. By incorporating the obtained polynucleotide into an expression vector known in the art, an expression vector containing a polynucleotide encoding a Fab fragment of the modified antibody of the present embodiment is obtained. By transforming or transfecting the obtained expression vector into an appropriate host cell, a Fab fragment of the modified antibody can be obtained.

Conventionally, a technique for modifying an affinity of an antibody for an antigen by introducing a mutation into an amino acid sequence of the antibody has been known. However, even if the affinity for the antigen has been modified as desired by introduction of the mutation, thermal stability of the antibody may be reduced at the same time. Since the thermal stability of the antibody correlates with storage stability and aggregation resistance of the antibody, it is used as one of indexes in development of antibody drugs. As described above, the modified antibody of the present embodiment binds to the same antigen as the unmodified antibody, and the affinity for the antigen is also similar to that of the unmodified antibody. Therefore, when the method for improving thermal stability of the present embodiment is applied to, for example, a mutant antibody in which affinity for an antigen is improved by introducing a mutation but thermal stability is reduced, the thermal stability can be improved while maintaining the affinity of the antibody for the antigen.

According to the method for producing a modified antibody of the present embodiment (hereinafter, also referred to as "production method"), the modified antibody of the present embodiment described above can be obtained. In the production method of the present embodiment, first, in a heavy chain of the antibody, at least one amino acid residue selected from the group consisting of the 8th to 11th amino acid residues based on the Kabat method is changed to a cysteine residue and at least one amino acid residue selected from the group consisting of the 109th and 110th amino acid residues based on the IMGT method is changed to a cysteine residue. The antibody whose heavy chain is modified in the production method of the present embodiment is the same as the unmodified antibody described above. Details of the method of changing the above amino acid residue in the heavy chain of the unmodified antibody to a cysteine residue are the same as those described for the method for improving thermal stability of the present embodiment.

Subsequently, the antibody obtained by the modification of the heavy chain is recovered. For example, a host cell expressing the modified antibody is dissolved in a solution containing an appropriate solubilizer to liberate the modified antibody in the solution. When the host cell secretes the modified antibody into a medium, a culture supernatant is recovered. The liberated modified antibody can be recovered by a known method such as affinity chromatography. For example, when the produced modified antibody is IgG, the antibody can be recovered by affinity chromatography using protein A or G. If necessary, the recovered modified antibody may be purified by a method known in the art such as gel filtration.

The scope of the present disclosure includes isolated and purified polynucleotides encoding a modified antibody of the present embodiment or fragments thereof. It is preferable that the isolated and purified polynucleotide encoding the fragment of the modified antibody of the present embodiment encodes a variable region of a heavy chain containing a cysteine residue at at least one position selected from positions 8 to 11 based on the Kabat method, and a constant region of a heavy chain containing a cysteine residue at at least one position selected from positions 109 and 110 based on the IMGT method. The scope of the present disclosure also includes a vector containing the above polynucleotide. A vector is a polynucleotide construct designed for transformation or transfection. The type of vector is not particularly limited. The vector can be appropriately selected from vectors known in the art such as expression vectors, cloning vectors, viral vectors and the like. The scope of the present disclosure also includes a host cell containing the vector. The type of the host cell is not particularly limited. The host cell can be appropriately selected from eukaryotic cells, prokaryotic cells, mammalian cells and the like.

The above method for improving thermal stability can be applied to an antibody which is an active ingredient of a known pharmaceutical composition. Another embodiment is a pharmaceutical composition containing the above modified antibody in a pharmacologically effective amount. For example, the heavy chain of the antibody contained in this pharmaceutical composition has CDR1: DTYIH (SEQ ID NO: 2), CDR2: RIYPTNGYTRYADSVKG (SEQ ID NO: 3) and CDR3: WGGDGFYAMDY (SEQ ID NO: 4). The heavy chain of the antibody may contain an amino acid sequence set forth in any of SEQ ID NOs: 6 to 13. The heavy chain of the antibody may contain an amino acid sequence of SEQ ID NO: 14. The antibody may further contain a light chain. For example, the light chain of the antibody has CDR1: RASQDVNTAVA (SEQ ID NO: 17), CDR2: SASFLYS (SEQ ID NO: 18) and CDR3: QQHYTTPPT (SEQ ID NO: 19). The light chain of the antibody may contain an amino acid sequence of SEQ ID NO: 15 or 16.

The pharmaceutical composition may contain pharmaceutically acceptable additives. Such additives can be appropriately selected from additives known in the art. Examples of the additives include excipients, lubricants, binders, disintegrants, coatings, capsule bases, plasticizers, colorants, solvents, stabilizers, preservatives, buffers, soothing agents, bases, emulsifiers, suspending agents, corrigents, sweeteners, absorbents, solubilizing agents, pH regulators, thickeners, tonicity agents, dispersants, preservatives, wetting agents, flavoring agents, antioxidants, and the like.

Formulation form of the pharmaceutical composition is not particularly limited, and may be any other formulation form known to those skilled in the art, such as a solid formulation, a semi-solid formulation, a liquid formulation, an injection, and a suppository. Specific dosage forms include, for example, tablets, pills, granules, powders, capsules, lozenges, injections, solutions, elixirs, syrups, limonades, suppositories, ointments, suspensions, emulsions, liniments, lotions, transdermal preparations, patches, cataplasms, aerosols, and the like, but are not limited thereto.

Another embodiment relates to a therapeutic method using the pharmaceutical composition described above. The treatment method of the present embodiment includes administering a pharmaceutical composition to a patient.

Hereinafter, the present disclosure will be described in more detail by examples, but the present disclosure is not limited to these examples.

EXAMPLES

Reference Example

From three-dimensional structural data of each of a mouse antibody, humanized antibody and rabbit antibody, amino acid residues where a variable region and a constant region are adjacent to each other in a heavy chain were found from each region, and distances between those amino acid residues were calculated by software.

(1) Adjacent Amino Acid Residues Between Variable Region and Constant Region

Amino acid sequences of heavy chains of each of a mouse anti-insulin antibody and a rabbit anti-CD80 antibody were input to Discovery Studio 2017 R2, and three-dimensional structure data of the heavy chains was obtained by automatic homology modeling function. Then, a three-dimensional structure of the heavy chain of each antibody was visualized. Three-dimensional structure data of a humanized anti-HER2 antibody (trastuzumab) was downloaded from Protein Data Bank (PDB), and the data was input to Discovery Studio 2017 R2 to visualize a three-dimensional structure of the heavy chain. As a result, it was found that, in the heavy chain of any antibody, a portion containing 8th to 11th amino acid residues in the variable region and a portion containing 108th to 111th amino acid residues in the constant region were adjacent to each other.

(2) Distance Between Adjacent Amino Acid Residues

Distances (Å) between α-carbon of each of the 8th to 11th amino acid residues of the variable region and α-carbon of each of the 108th to 111th amino acid residues of the constant region were calculated by Discovery Studio 2017 R2 based on the three-dimensional structural data. The results are shown in Tables 10 to 12.

TABLE 10

Mouse anti-insulin antibody

| Type and position of amino acid residue | | His 108 | Pro 109 | Ala 110 | Ser 111 |
|---|---|---|---|---|---|
| Gly | 8 | 10.697 | 7.489 | 8.566 | 11.850 |
| Pro | 9 | 9.920 | 7.408 | 7.186 | 10.931 |
| Glu | 10 | 11.755 | 9.226 | 7.396 | 11.014 |
| Leu | 11 | 12.408 | 10.689 | 7.739 | 10.792 |

TABLE 11

Humanized anti-HER2 antibody

| Position and type of amino acid residue | | His 108 | Lys 109 | Pro 110 | Ser 111 |
|---|---|---|---|---|---|
| Gly | 8 | 14.154 | 10.766 | 10.237 | 13.687 |
| Gly | 9 | 12.175 | 9.443 | 8.546 | 12.347 |
| Gly | 10 | 10.446 | 8.793 | 6.016 | 9.701 |
| Leu | 11 | 12.086 | 10.677 | 7.364 | 10.222 |

TABLE 12

Rabbit anti-CD80 antibody

| Position and type of amino acid residue | | His 108 | Pro 109 | Ala 110 | Thr 111 |
|---|---|---|---|---|---|
| Gly | 8 | 15.405 | 12.396 | 11.32 | 14.806 |
| Gly | 9 | 13.749 | 11.442 | 9.994 | 13.704 |
| Arg | 10 | 11.443 | 9.933 | 7.429 | 10.850 |
| Leu | 11 | 12.565 | 11.443 | 8.133 | 10.719 |

As shown by bold frames in Tables 10 to 12, it was found that, in the heavy chain of any antibody, each of the 8th to 11th amino acid residues based on the Kabat method and each of the 109th and 110th amino acid residues based on the IMGT method were more adjacent to each other.

Example 1: Preparation of Modified Antibody

For each of the humanized antibody, mouse antibody and rabbit antibody, the amino acid residues specified in the above reference example were substituted with cysteine residues to prepare a modified antibody so as to form a disulfide bond between the variable region and the constant region.

(1) Acquisition of Gene of Each Antibody (1.1) Acquisition of Gene of Humanized Antibody A gene of a humanized anti-HER2 monoclonal antibody (trastuzumab) was synthesized by GenScript Japan Inc. on commission, so that a plasmid DNA containing the gene of the humanized anti-HER2 antibody was acquired.

(1.2) Acquisition of Gene of Mouse Antibody

A gene of a mouse anti-insulin antibody was acquired in the following manner.

[Reagents]
ISOGEN (NIPPON GENE CO., LTD.)
SMARTer (registered trademark) RACE 5'/3' kit (clontech)
10× A-attachment mix (TOYOBO CO., LTD.)
pcDNA (trademark) 3.4 TOPO (registered trademark) TA cloning kit (Thermo Fisher Scientific K.K.)
Competent high DH5α (TOYOBO CO., LTD.)
QIAprep Spin Miniprep kit (QIAGEN)
KOD plus neo (TOYOBO CO., LTD.)
Ligation high ver.2 (TOYOBO CO., LTD.)

(i) Extraction of Total RNA from Antibody-Producing Hybridoma

Hybridomas that produce a mouse anti-human insulin antibody were prepared by using human insulin as an antigen, according to the method described in Kohler and Milstein, Nature, vol. 256, p. 495-497, 1975. The hybridoma culture (10 mL) was centrifuged at 1000 rpm for 5 minutes, then the supernatant was removed. The resulting cells were dissolved with ISOGEN (1 mL). The solution was allowed to stand at room temperature for 5 minutes. Chloroform (200 μL) was added thereto, and the mixture was stirred for 15 seconds. Then, the mixture was allowed to stand at room temperature for 3 minutes. Then, this was centrifuged at 12000×G at 4° C. for 10 minutes, and an aqueous phase (500 μL) containing RNA was recovered. Isopropanol (500 μL) was added to the recovered aqueous phase, and the mixture was mixed. The resulting mixture was allowed to stand at room temperature for 5 minutes. Thereafter, the resulting mixture was centrifuged at 12000×G at 4° C. for 10 minutes. The supernatant was removed, and 70% ethanol (1 mL) was added to the resulting precipitate (total RNA). The mixture was centrifuged at 7500×G at 4° C. for 10 minutes. The supernatant was removed, and RNA was air-dried. The RNA was dissolved in RNase-free water (20 μL).

(ii) Synthesis of cDNA

Using each of the total RNAs obtained in the above (i), RNA samples having the following composition were prepared.

| [RNA Sample] | |
|---|---|
| Total RNA (500 ng/μL) | 1 μL |
| RT Primer | 1 μL |
| Deionized water | 1.75 μL |
| Total | 3.75 μL |

The prepared RNA sample was heated at 72° C. for 3 minutes. Thereafter, the RNA sample was incubated at 42° C. for 2 minutes. Then, a cDNA synthesis sample was prepared by adding 12 μM SMARTer II A oligonucleotide (1 μL) to the RNA sample. Using this cDNA synthesis sample, a reverse transcription reaction solution having the following composition was prepared.

| [Reverse Transcription Reaction Solution] | |
|---|---|
| 5× First-Strand buffer | 2 μL |
| 20 mM DTT | 1 μL |
| 10 mM dNTP mix | 1 μL |
| RNase inhibitor | 0.25 μL |
| SMARTScribe RT(100 U/μL) | 1 μL |
| cDNA synthesis sample | 4.75 μL |
| Total | 10 μL |

The prepared reverse transcription reaction solution was reacted at 42° C. for 90 minutes. Then, the reaction solution was heated at 70° C. for 10 minutes, and tricine-EDTA (50 μL) was added thereto. Using the obtained solution as a cDNA sample, a 5'RACE reaction solution having the following composition was prepared.

| [5'RACE Reaction Solution] | |
|---|---|
| 10× PCR buffer | 5 μL |
| dNTP mix | 5 μL |
| 25 mM Mg$_2$SO$_4$ | 3.5 μL |
| cDNA sample | 2.5 μL |
| 10× Universal Primer Mix | 5 μL |
| 3'-Primer | 1 μL |
| KOD plus neo (1 U/μL) | 1 μL |
| Purified water | 27 μL |
| Total | 50 μL |

The prepared 5'RACE reaction solution was subjected to RACE reaction under the following reaction conditions. The following "t" is 90 seconds for the light chain and 150 seconds for the heavy chain.

[Reaction Conditions]

At 94° C. for 2 minutes, 30 cycles at 98° C. for 10 seconds, 50° C. for 30 seconds, and 68° C. for t seconds, and at 68° C. for 3 minutes.

Using the 5'RACE product obtained in the above reaction, a solution having the following composition was prepared. The solution was reacted at 60° C. for 30 minutes, and adenine was added to the end of the 5'RACE product.

| | |
|---|---|
| 5'RACE product | 9 μL |
| 10× A-attachment mix | 1 μL |
| Total | 10 μL |

A TA cloning reaction solution having the following composition was prepared using the resulting adenine addition product and pcDNA (trade name) 3.4 TOPO (registered trademark) TA cloning kit. The reaction solution was incubated at room temperature for 10 minutes, and the adenine adduct was cloned into pcDNA3.4.

| [TA Cloning Reaction Solution] | |
|---|---|
| Adenine adduct | 4 μL |
| salt solution | 1 μL |
| pCDNA3.4 | 1 μL |
| Total | 6 μL |

(iii) Transformation, Plasmid Extraction and Sequence Confirmation

The TA cloning sample (3 μL) obtained in the above (ii) was added to DH5α (30 μL), and the mixture was allowed to stand on ice for 30 minutes. Thereafter, the mixture was heat shocked by heating at 42° C. for 45 seconds. The mixture was again allowed to stand on ice for 2 minutes, then the whole amount was applied to an ampicillin-containing LB plate. The plate was incubated at 37° C. for 16 hours. Single colonies on the plate were placed in the ampicillin-containing LB liquid medium, and the medium was shake-cultured (250 rpm) at 37° C. for 16 hours. The culture was centrifuged at 5000×G for 5 minutes to recover E. coli transformants. Plasmids were extracted from the recovered E. coli using the QIAprep Spin Miniprep kit. Specific operations were carried out according to the manual attached to the kit. A base sequence of the obtained plasmid was confirmed using pcDNA3.4 vector primer. From the above, a plasmid DNA containing the gene of the mouse anti-insulin antibody was acquired.

(1.3) Acquisition of Gene of Rabbit Antibody

Lymphocytes were acquired from peripheral blood of a rabbit immunized with CD80, and mRNA was extracted from the lymphocytes to synthesize cDNA. The obtained cDNA was amplified using a known primer for cloning an antibody gene to prepare a Fab phage library. Using the obtained library, a Fab clone of a rabbit anti-CD80 antibody was obtained by a known Fab phage display method and biopanning (see Lang IM, Barbas CF 3rd, Schleef RR., Recombinant rabbit Fab with binding activity to type-1 plasminogen activator inhibitor derived from a phage-display library against human alpha-granules, (1996) Gene 172(2): 295-8 and Philippa M. O'Brien, Robert Aitken, Antibody Phage Display, (2002) Methods in Molecular Biology Volume No. 178). A gene of the acquired Fab clone of the rabbit anti-CD80 antibody was incorporated into a plasmid DNA containing a gene encoding a Fc region of the rabbit antibody to acquire a plasmid DNA containing the gene of the rabbit anti-CD80 antibody.

(2) Acquisition of Genes of Mutant Types of Each Antibody (2.1) Primer Design and PCR A primer for substituting a 9th or 10th amino acid residue of a variable region with a cysteine residue and substituting a 109th or 110th amino acid residue of a constant region in a heavy chain with a cysteine residue based on a base sequence of a gene of each antibody was designed. In order to further introduce into each antibody a mutation to a light chain described in U.S. Patent Application Publication No. 2019/0040119, a primer for substituting a 80th amino acid residue in a variable region with a cysteine residue and substituting a 171st amino acid residue in a constant region in a light chain of each antibody with a cysteine residue was designed.

Using the plasmid DNA containing the gene of each antibody as a template, a PCR reaction solution having the following composition was prepared.

| [PCR Reaction Solution] | |
|---|---|
| 10x PCR buffer | 5 μL |
| 25 mM Mg$_2$SO$_4$ | 3 μL |
| 2 mM dNTP mix | 5 μL |
| Forward primer | 1 μL |

-continued

| [PCR Reaction Solution] | |
|---|---|
| Reverse primer | 1 μL |
| Plasmid DNA (40 ng/μL) | 0.5 μL |
| KOD plus neo (1 U/μL) | 1 μL |
| Purified water | 33.5 μL |
| Total | 50 μL |

The prepared PCR reaction solution was subjected to a PCR reaction under the following reaction conditions.

[Reaction Conditions]

30 cycles at 98° C. for 2 minutes, 98° C. for 10 seconds, 54° C. for 30 seconds and 68° C. for 4 minutes, and at 68° C. for 3 minutes.

The obtained PCR product was fragmented by adding 2 μL of DpnI (10 U/μL) to the PCR product (50 μL). Using the DpnI-treated PCR product, a ligation reaction solution having the following composition was prepared. The reaction solution was incubated at 16° C. for 1 hour to perform a ligation reaction.

| [Ligation Reaction Liquid] | |
|---|---|
| DpnI-treated PCR product | 2 μL |
| Ligation high ver.2 | 5 μL |
| T4 Polynucleotide kinase | 1 μL |
| Purified water | 7 μL |
| Total | 15 μL |

(2.2) Transformation, Plasmid DNA Extraction and Sequence Confirmation

A solution (3 μL) after the ligation reaction was added to DH5α (30 μL), and E. coli transformants were obtained in the same manner as in the above (1.2) (iii). Plasmids DNA were extracted from the obtained E. coli using the QIAprep Spin Miniprep kit. The base sequence of each obtained plasmid DNA was confirmed using pcDNA 3.4 vector primer. Hereinafter, these plasmids DNA were used as plasmids for expressing mammalian cells.

(3) Expression in Mammalian Cells

[Reagents]
Expi293 (trademark) cells (Invitrogen)
Expi293 (trademark) Expression medium (Invitrogen)
ExpiFectamine (trademark) 293 transfection kit (Invitrogen)

(3.1) Transfection

Expi293 cells were proliferated by shaking culture (150 rpm) at 37° C. in a 5% $CO_2$ atmosphere. 30 mL of cell culture (3.0×10$^6$ cells/mL) was prepared according to the number of samples. A DNA solution having the following composition was prepared using a plasmid DNA encoding wild type and mutant type of each antibody. The DNA solution was allowed to stand for 5 minutes.

| [DNA Solution] | |
|---|---|
| Light chain plasmid solution | Amount (μL) corresponding to 15 μg |
| Heavy chain plasmid solution | Amount (μL) corresponding to 15 μg |
| Opti-MEM (trademark) | Appropriate amount (mL) |
| Total | 1.5 mL |

A transfection reagent having the following composition was prepared. The transfection reagent was allowed to stand for 5 minutes.

| | |
|---|---|
| ExpiFectamine reagent | 80 µL |
| Plasmid solution | 1420 µL |
| Total | 1.5 mL |

The prepared DNA solution and the transfection reagent were mixed. The mixture was allowed to stand for 20 minutes. The resulting mixture (3 mL) was added to the cell culture (30 mL). The mixture was shake-cultured (150 rpm) at 37° C. for 20 hours in a 5% $CO_2$ atmosphere. After 20 hours, 150 µL and 1.5 mL of ExpiFectamine (trademark) transfection enhancers 1 and 2 were added to each culture, respectively. Each mixture was shake-cultured (150 rpm) at 37° C. for 6 days in a 5% $CO_2$ atmosphere.

(3.2) Recovery and Purification of Antibody

Each cell culture was centrifuged at 3000 rpm for 5 minutes, and the culture supernatant was recovered. The culture supernatant contains each antibody secreted from transfected Expi293 (trademark) cells. The obtained culture supernatant was again centrifuged at 15000×G for 10 minutes, and the supernatant was recovered. The obtained supernatant was purified using a HiTrap Protein A HP column (GE Healthcare). The obtained solution was further purified using a Superdex 200 Increase 10/300 GL column (GE Healthcare) to obtain an antibody solution. A specific procedure for purification was carried out in accordance with an attached document of each column.

(4) Results

A wild type of the humanized anti-HER2 antibody (trastuzumab) and a heavy-chain mutant type (9-109), a heavy-chain mutant type (10-110) and a light-chain/heavy-chain mutant type (80-171/10-110) as modified antibodies thereof were obtained. The wild type of the humanized anti-HER2 antibody has a heavy chain containing an amino acid sequence represented by SEQ ID NO: 1. The heavy-chain mutant type (9-109) and heavy-chain mutant type (10-110) of the humanized anti-HER2 antibody have a heavy chain containing an amino acid sequence represented by SEQ ID NO: 8 and a heavy chain containing an amino acid sequence represented by SEQ ID NO: 11, respectively. The light-chain/heavy-chain mutant type (80-171/10-110) of the humanized anti-HER2 antibody has the heavy chain containing the amino acid sequence represented by SEQ ID NO: 11 and a light chain containing an amino acid sequence represented by SEQ ID NO: 16.

A wild type of the rabbit anti-CD80 antibody and a heavy-chain mutant type (9-109), a heavy-chain mutant type (9-110), a heavy-chain mutant type (10-110), a light-chain/heavy-chain mutant type (80-171/9-109) and a light-chain/heavy-chain mutant type (80-171/9-110) as modified antibodies thereof were obtained. The wild type of the rabbit anti-CD80 antibody has a heavy chain containing an amino acid sequence represented by SEQ ID NO: 21. The heavy-chain mutant type (9-109), heavy-chain mutant type (9-110) and heavy-chain mutant type (10-110) of the rabbit anti-CD80 antibody have a heavy chain containing an amino acid sequence represented by SEQ ID NO: 24, a heavy chain containing an amino acid sequence represented by SEQ ID NO: 25, and a heavy chain containing an amino acid sequence represented by SEQ ID NO: 27, respectively. The light-chain/heavy-chain mutant type (80-171/9-109) of the rabbit anti-CD80 antibody has the heavy chain containing the amino acid sequence represented by SEQ ID NO: 24 and a light chain containing an amino acid sequence represented by SEQ ID NO: 31. The light-chain/heavy-chain mutant type (80-171/9-110) of the rabbit anti-CD80 antibody has the heavy chain containing the amino acid sequence represented by SEQ ID NO: 25 and the light chain containing the amino acid sequence represented by SEQ ID NO: 31.

A wild type of the mouse anti-insulin antibody, and a heavy-chain mutant type (9-109), a heavy-chain mutant type (10-110), a light-chain/heavy-chain mutant type (80-171/9-109) and a light-chain/heavy-chain mutant type (80-171/10-110) as modified antibodies thereof were obtained. The heavy-chain mutant type (9-109) of the mouse anti-insulin antibody is an antibody in which a 9th amino acid residue of a variable region based on Kabat method has been substituted with a cysteine residue and a 109th amino acid residue of a constant region based on IMGT method in a heavy chain of the wild-type antibody has been substituted with a cysteine residue. The heavy-chain mutant type (10-110) of the mouse anti-insulin antibody is an antibody in which a 10th amino acid residue of a variable region based on the Kabat method has been substituted with a cysteine residue and a 110th amino acid residue of a constant region based on the IMGT method in a heavy chain of the wild-type antibody has been substituted with a cysteine residue. The light-chain/heavy-chain mutant type (80-171/10-110) of the mouse anti-insulin antibody is an antibody in which the 9th amino acid residue of the variable region based on the Kabat method has been substituted with a cysteine residue and the 109th amino acid residue in the constant region based on the IMGT method in the heavy chain of the wild-type antibody has been substituted with a cysteine residue, and the 80th amino acid residue in the variable region has been substituted with a cysteine residue and the 171st amino acid residue in the constant region based on the Kabat method in the light chain of the wild-type antibody has been substituted with a cysteine residue.

Example 2: Thermal Stability of Modified Antibody

Thermal stability of the wild type of each antibody prepared in Example 1 and modified antibodies thereof were examined.

(1) Measurement of Thermal Stability

Fab fragments were obtained from each antibody obtained in Example 1 by a conventional method. A solvent of the solution containing the Fab fragment of each antibody was substituted with a buffer (phosphate buffered saline: PBS) used for measurement with a differential scanning calorimeter (DSC) by gel filtration. The conditions of gel filtration are as follows.

[Conditions of Gel Filtration]
  Buffer: PBS (pH 7.4)
  Used column: Superdex 200 Increase 10/300 (GE Healthcare)
  Column volume (CV): 24 mL
  Sample volume: 500 µL
  Flow rate: 1.0 mL/min
  Elution amount: 1.5 CV
  Fraction volume: 500 µL Fractions containing the Fab fragment of each antibody were diluted with PBS to prepare samples (final concentration 5 µM). Tm values of the Fab fragments of each antibody were measured using MicroCal PEAQ-DSC (Malvern Instruments Ltd.). Measurement conditions are as follows.

[DSC Measurement Conditions]
  Sample amount: 400 µL
  Measurement range: 30° C. to 100° C.
  Temperature elevation rate: 1° C./min (2) Results The Tm values of each antibody obtained by DSC measurement are shown in Tables 13 to 15 below. In the table, "ΔTm (° C.)" is a difference between the Tm value of each mutant type and the Tm value of the wild type.

TABLE 13

| Mouse anti-insulin antibody (Fab) | Tm (° C.) | ΔTm (° C.) |
|---|---|---|
| Wild type | 77.1 | — |
| Heavy-chain mutant type (9-109) | 79.3 | 2.2 |
| Heavy-chain mutant type (10-110) | 79.2 | 2.1 |
| Light-chain/heavy-chain mutant type (80-171/9-109) | 83.3 | 6.2 |
| Light-chain/heavy-chain mutant type (80-171/10-110) | 83.0 | 5.9 |

TABLE 14

| Humanized anti-HER2 antibody (Fab) | Tm (° C.) | ΔTm (° C.) |
|---|---|---|
| Wild type | 81.9 | — |
| Heavy-chain mutant type (9-109) | 83.8 | 1.9 |
| Heavy-chain mutant type (10-110) | 86.0 | 4.1 |
| Light-chain/heavy-chain mutant type (80-171/10-110) | 89.7 | 7.8 |

TABLE 15

| Rabbit anti-CD80 antibody (Fab) | Tm (° C.) | ΔTm (° C.) |
|---|---|---|
| Wild type | 79.8 | — |
| Heavy-chain mutant type (9-109) | 82.1 | 2.3 |
| Heavy-chain mutant type (10-110) | 83.5 | 3.7 |
| Heavy-chain mutant type (9-110) | 82.8 | 3.0 |
| Light-chain/heavy-chain mutant type (80-171/9-109) | 85.3 | 5.5 |
| Light-chain/heavy-chain mutant type (80-171/9-110) | 86.8 | 7.0 |

As shown in Tables 13 to 15, the Tm value of any of the modified antibodies of the humanized antibody, the mouse antibody and the rabbit antibody were higher than that of the wild type of each antibody by about 2 to 4° C. Therefore, it was shown that the modified antibody of the present embodiment is an antibody with improved thermal stability as compared to an original antibody. The Tm value of the light-chain/heavy-chain mutant type was higher than that of the wild type by 5° C. or more. From this, it was shown that the thermal stability can be further improved by modifying the antibody so that a disulfide bond is formed not only in the heavy chain but also in the light chain.

Example 3: Aggregating Properties of Modified Antibody

Aggregating properties of the wild type and modified antibodies of the humanized anti-HER2 antibody were examined. As the modified antibodies, the light-chain/heavy-chain mutant type (80-171/10-110) prepared in Example 1 and the light-chain mutant type (80-171) prepared using a primer set for light chain modification of Example 1 were used.

(1) Measurement of Diffusion Coefficient

The solvent of the solution containing each antibody was substituted with PBS (pH 7.4) by gel filtration. Fractions containing each antibody were diluted with PBS to prepare samples (final concentration 12.5 to 100 μM). Diffusion coefficient of each antibody was measured at 25° C. by dynamic light scattering (DLS) method using Zetasizer Nano ZSP (Malvern Panalytical Ltd). From the DLS measurement results, the antibody concentration was plotted on an x-axis, and the diffusion coefficient (μm²/s) was plotted on a y-axis. A regression line of the plotted data was calculated by a least squares method, and slope and intercept of the regression line were obtained. In the least squares method, a and b that minimize a value of $\Sigma\{yk-(a \times k+b)\}^2$ were obtained.

(2) Measurement of THERMAL stability

The solvent of the solution containing each antibody was substituted with PBS (pH 7.4) by gel filtration. Fractions containing each antibody were diluted with PBS to prepare samples (final concentration 5 μM). Tm values of each antibody were measured using MicroCal PEAQ-DSC (Malvern Instruments Ltd.). Conditions for gel filtration and DSC measurement were the same as those described in Example 1.

(3) Results

Equations of the regression lines for each antibody are shown in Table 16 below. In the table, "ΔTm (° C.)" is a difference between the Tm value of each mutant type and the Tm value of the wild type. The term "aggregating properties" indicates a result of evaluating a change in aggregating properties of each mutant type with respect to the wild-type antibody based on the value of the slope of the regression line.

TABLE 16

| Humanized anti-HER2 antibody | ΔTm (° C.) | Regression line | Aggregating properties |
|---|---|---|---|
| Wild type | 0 | y = −1.7x + 68.8 | — |
| Light-chain mutant type (80-171) | +3.4 | y = −1.6x + 69.8 | No change |
| Light-chain/heavy-chain mutant type (80-171/10-110) | +7.8 | y = −0.9x + 68.3 | Improved |

In the regression line in a graph plotting the antibody concentration and the diffusion coefficient, it is known that the closer the value of the slope is to 0, the more dispersed the antibody in the solution is. As can be seen from Table 16, the aggregating properties of the light-chain mutant type (80-171) was almost the same as that of the wild type, but the aggregating properties of the light-chain/heavy-chain mutant type (80-171/10-110) was improved more than those of the wild type. From this result, it was suggested that the aggregating properties could be improved by modifying both the heavy chain and the light chain.

Example 4: Affinity of Modified Antibody for Antigen

Affinities of the wild type of each antibody and the mutant type thereof prepared in Example 1 for an antigen were examined by ELISA method.

(1) Measurement by ELISA Method (1.1) Antigen and Antibody for Detection

HER2 protein (R&D Systems, Inc., catalog number: 1129-ER) was used as an antigen for a human anti-HER2 antibody. Humulin R U-100 (Eli Lilly and Company) was used as an antigen for a mouse anti-insulin antibody. CD80 protein (R&D Systems, Inc., catalog number: 140-B1) was used as an antigen for a rabbit anti-CD80 antibody. As antibodies for detection, the wild type and the heavy-chain mutant type (10-110) of the humanized anti-HER2 antibody (Fab), the wild type and the heavy-chain mutant type (9-109) of the mouse anti-insulin antibody (Fab), and the wild type and the heavy-chain mutant type (9-109) of the rabbit anti-CD80 antibody (Fab) were used. A histidine tag was added to these antibodies for detection (Fabs). Each antibody for detection was stepwise diluted with 1% BSA-containing PBS to obtain a plurality of Fab solutions with different concentrations.

(1.2) Measurement

Each antigen was diluted with PBS (pH 7.4) to prepare a solution of each antigen. The solution of each antigen was added to wells of a MaxiSorp (trademark) flat bottom plate (Thermo Fisher Scientific, Inc.). The mixture was allowed to stand overnight at 4° C. The antigen solution was removed, and a blocking solution (1% BSA-containing PBS) was added to each well to perform blocking. After removing the blocking solution, 100 μL of each Fab solution was added to each well, and an antigen-antibody reaction was carried out at room temperature for 1 hour. The Fab solution was removed, and a washing liquid (1% BSA-containing PBS) was added to each well to wash the wells. After washing, a solution of a HRP-labeled anti-His Tag antibody (Bethyl Laboratories, Inc., catalog number: A190-114P) was added, and an antigen-antibody reaction was carried out at room temperature. The antibody solution was removed, and a washing liquid (1% BSA-containing PBS) was added to each well to wash the wells. After washing, a solution of an ABST substrate (Thermo Fisher Scientific Inc.) was added to each well, and absorbance at 450 nm was measured. The results are shown in FIGS. 1 to 3.

(2) Results

Figure 2:
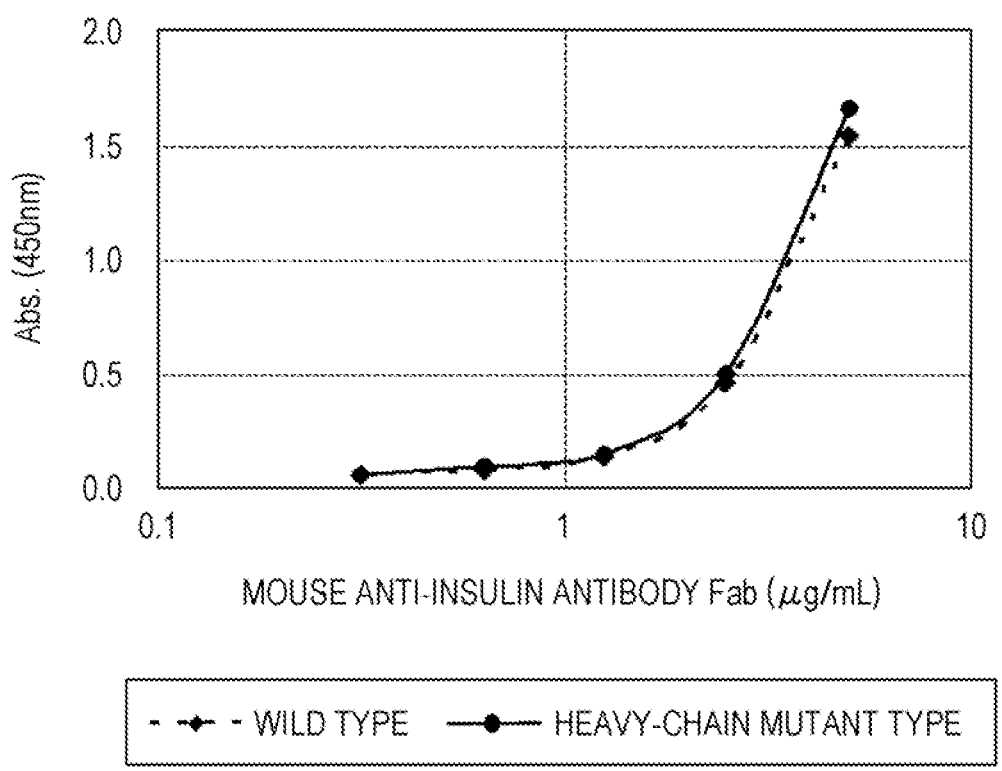
FIG. 2 is a graph showing results of analyzing affinities of a wild type and a heavy-chain mutant type (9-109) of a mouse anti-insulin antibody (Fab) for an antigen by ELISA method.
Figure 3:
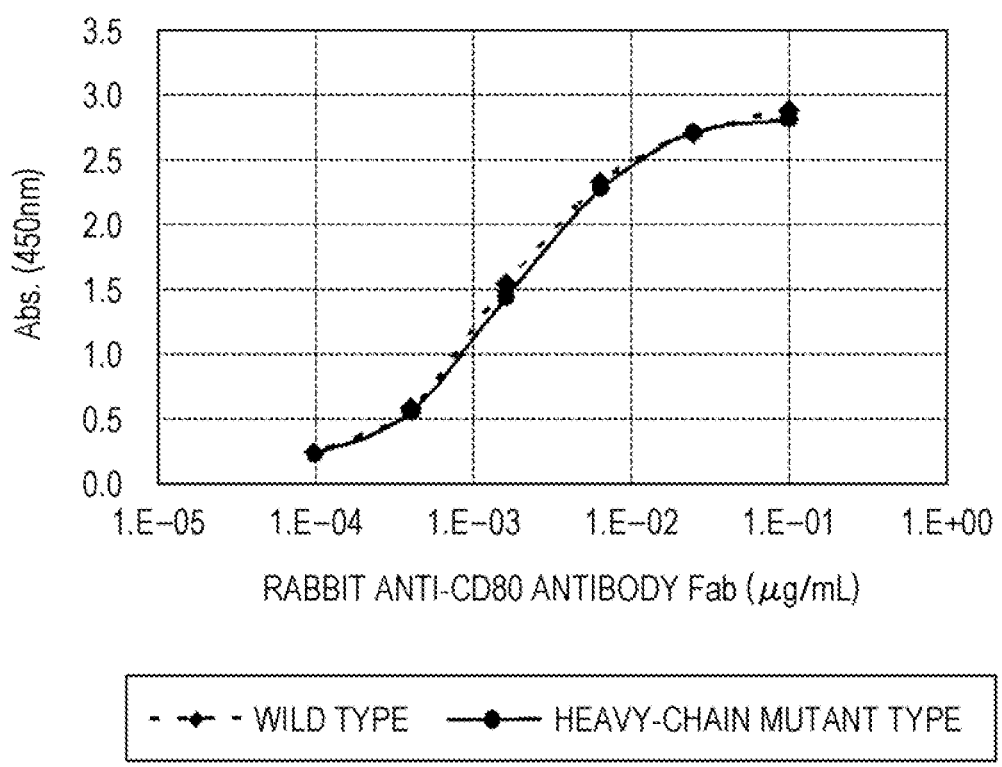
FIG. 3 is a graph showing results of analyzing affinities of a wild type and a heavy-chain mutant type (9-109) of a rabbit anti-CD80 antibody (Fab) for an antigen by ELISA method.

As shown in FIGS. 1 to 3, the affinity for the antigen in any of the modified antibodies of the humanized antibody, the mouse antibody and the rabbit antibody were almost the same as that in the wild type of each antibody.

What is claimed is:

1. A method for improving thermal stability of an antibody, comprising:
   in a heavy chain of the antibody, changing at least one amino acid residue selected from the group consisting of 8th to 11th amino acid residues based on Kabat method to a cysteine residue, and changing at least one amino acid residue selected from the group consisting of 109th and 110th amino acid residues based on IMGT method to a cysteine residue,
   wherein the modified antibody has improved thermal stability as compared to the unmodified antibody; and
   wherein the modified antibody is Fab, Fab', F(ab')2, reduced IgG, IgG, IgA, IgM, IgD or IgE.

2. The method according to claim 1, wherein the changing step comprises substituting the at least one amino acid residue selected from the group consisting of the 8th to 11th amino acid residues to a cysteine residue.

3. The method according to claim 1, wherein the changing step comprises substituting the at least one amino acid residue selected from the group consisting of the 109th and 110th amino acid residues to a cysteine residue.

4. The method according to claim 1, wherein the changing step comprises changing at least one amino acid residue selected from the group consisting of 9th and 10th amino acid residues based on the Kabat method to a cysteine residue.

5. The method according to claim 1, wherein the changing step comprises substituting at least one amino acid residue selected from the group consisting of 9th and 10th amino acid residues based on the Kabat method to a cysteine residue.

6. The method according to claim 1, wherein the changing step comprises changing amino acid residues selected from the group consisting of 1) to 3) below to cysteine residues,
   1) The 9th amino acid residue based on the Kabat method and the 109th amino acid residue based on the IMGT method;
   2) The 9th amino acid residue based on the Kabat method and the 110th amino acid residue based on the IMGT method; and
   3) The 10th amino acid residue based on the Kabat method and the 110th amino acid residue based on the IMGT method.

7. The method according to claim 1, wherein a disulfide bond is formed between the cysteine residue at any position of 8 to 11 based on the Kabat method and the cysteine residue at any position of 109 and 110 based on the IMGT method.

8. The method according to claim 1, further comprising: in a light chain of the antibody, changing 80th and 171st amino acid residues based on the Kabat method to cysteine residues.

9. The modified antibody according to claim 8, wherein a disulfide bond is formed between the cysteine residues at positions 80 and 171 based on the Kabat method.

10. A method for producing a modified antibody, comprising:
    in a heavy chain of the antibody, changing at least one amino acid residue selected from the group consisting of 8th to 11th amino acid residues based on Kabat method to a cysteine residue, and changing at least one amino acid residue selected from the group consisting of 109th and 110th amino acid residues based on IMGT method to a cysteine residue;
    wherein a disulfide bond is formed between the cysteine residue at any position of 8 to 11 based on the Kabat method and the cysteine residue at any position of 109 and 110 based on the IMGT method;
    wherein the modified antibody is Fab, Fab', F(ab')2, reduced IgG, IgG, IgA, IgM, IgD or IgE, and
    recovering the modified antibody.

11. The method according to claim 10, wherein the changing step comprises substituting the at least one amino acid residue selected from the group consisting of the 8th to 11th amino acid residues to a cysteine residue.

12. The method according to claim 10, wherein the changing step comprises substituting the at least one amino acid residue selected from the group consisting of the 109th and 110th amino acid residues to a cysteine residue.

13. The method according to claim 10, wherein the changing step comprises changing at least one amino acid residue selected from the group consisting of 9th and 10th amino acid residues based on the Kabat method to a cysteine residue.

14. The method according to claim 10, wherein the changing step comprises substituting at least one amino acid residue selected from the group consisting of 9th and 10th amino acid residues based on the Kabat method to a cysteine residue.

15. The method according to claim 10, wherein the changing step comprises changing amino acid residues selected from the group consisting of 1) to 3) below to cysteine residues,
   1) The 9th amino acid residue based on the Kabat method and the 109th amino acid residue based on the IMGT method;
   2) The 9th amino acid residue based on the Kabat method and the 110th amino acid residue based on the IMGT method; and
   3) The 10th amino acid residue based on the Kabat method and the 110th amino acid residue based on the IMGT method.

16. The method according to claim 10, further comprising: in a light chain of the antibody, changing 80th and 171st amino acid residues based on the Kabat method to cysteine residues.

17. The modified antibody according to claim 16, wherein a disulfide bond is formed between the cysteine residues at positions 80 and 171 based on the Kabat method.

* * * * *